(12) United States Patent
Horn et al.

(10) Patent No.: US 8,278,118 B2
(45) Date of Patent: Oct. 2, 2012

(54) METHOD FOR THE FRACTIONATION AND SEPARATION OF PARTICLES BY STEP-WISE GRADIENT DENSITY EXTRACTION

(75) Inventors: Marcus Joseph Horn, Parsippany, NJ (US); Wenkui Lan, Livingston, NJ (US)

(73) Assignee: Prospect Biosystems, Inc., Newark, NJ (US)

( * ) Notice: Subject to any disclaimer, the term of this patent is extended or adjusted under 35 U.S.C. 154(b) by 475 days.

(21) Appl. No.: 12/380,907

(22) Filed: Mar. 5, 2009

(65) Prior Publication Data

US 2009/0265184 A1 Oct. 22, 2009

Related U.S. Application Data

(63) Continuation-in-part of application No. 11/441,934, filed on May 26, 2006.

(51) Int. Cl.
G01N 1/18 (2006.01)
B01D 21/26 (2006.01)

(52) U.S. Cl. ............ 436/177; 436/63; 436/71; 210/787; 210/800; 210/781; 494/37

(58) Field of Classification Search ................ 210/781, 210/782, 787, 808, 805, 789, 800, 806, 790, 210/768; 436/45, 52, 177, 6, 713; 422/72, 422/101; 494/37, 28.3, 16
See application file for complete search history.

(56) References Cited

U.S. PATENT DOCUMENTS

| | | | | |
|---|---|---|---|---|
| 4,096,035 | A | * | 6/1978 | Machlowitz et al. ...... 435/252.1 |
| 4,177,921 | A | * | 12/1979 | Nielsen .............................. 494/1 |
| 4,648,863 | A | * | 3/1987 | Nees ................................ 494/17 |

(Continued)

FOREIGN PATENT DOCUMENTS
WO 9851412 11/1998

OTHER PUBLICATIONS

Evans et al., Effect of storage at 4C and -20C on lipid, lipoprotein, and apolipoprotein concentrations, 1995, Clinical Chemistry, vol. 41, No. 3, pp. 392-396.*

(Continued)

*Primary Examiner* — Tony G Soohoo
*Assistant Examiner* — David C Mellon

(74) *Attorney, Agent, or Firm* — Lowenstein Sandler PC

(57) ABSTRACT

A method for the separation of particles of different densities using a step-wise gradient density extraction method as described herein where a sample is suspended in a liquid volume of an extracting medium of specific density and the particles that have a density less than or equal to that of the extracting medium of specific density can be recovered from a horizonatally rotatable hollow disk or a removable receptacle within a horizontally rotatable hollow disk designed for such purposes while the particles that have a density greater than the extracting medium of specific density form a deposit which can be cycled through the extraction process in an iterative fashion by varying the density of the extracting medium allowing the recovery of discrete particles of differing densities from a test sample. Also disclosed herein is the use of the above method as part of a separate method or system to identify a ratio of biomarkers from different fractions of a sample homogenate or lysate which is useful in the evaluation of potential biomarkers, and for the intraoperative pathological diagnosis of positive margins of cancer and other diseases.

51 Claims, 16 Drawing Sheets

U.S. PATENT DOCUMENTS

| | | | | |
|---|---|---|---|---|
| 4,939,087 | A | * | 7/1990 | Van Wie et al. .............. 435/394 |
| 5,403,745 | A | * | 4/1995 | Ollington et al. .............. 435/11 |
| 5,786,898 | A | * | 7/1998 | Fitzpatrick .................... 356/426 |
| 6,652,136 | B2 | * | 11/2003 | Marziali ....................... 366/235 |
| 6,821,757 | B2 | | 11/2004 | Sauer et al. |
| 2002/0131894 | A1 | * | 9/2002 | Anderson ...................... 422/61 |
| 2007/0272612 | A1 | | 11/2007 | Horn et al. |
| 2009/0265184 | A1 | * | 10/2009 | Horn et al. ....................... 705/2 |

OTHER PUBLICATIONS

Weiller et al., Analysis of lipoproteins by capillary zone electrophoresis in microfluidic devices, assay development and surface roughness measurements, Apr. 1, 2002, Analytical Chemistry, vol. 74, No. 7, pp. 1702-1711.*

Pafko, W., "Centrifuge Settling & Filtration Theory", Centrifuge Settling & Filtration Theory, Chapter XII, Special Topics Report at www.pafko.com/wayne/docs/centrifuge.pdf.

Pretlow II, T.G. et al "Velocity Sedimentation of Organelles at Low Centrifugal Force in an Isokinetic Gradient", Biochem. J., (1978), 174: 303-307.

Rickwood, D., "Centrifugation: A Practical Approach", Centrifugation: A Practical Approach, IRL Press, Oxford University, (1992).

Written Opinion of the International Searching Authority for International Patent Application No. PCT/US2007/010538 issued Oct. 8, 2008.

International Search Report for International Patent Application No. PCT/US2007/010538 issued Oct. 8, 2008.

de Almeida, M., et al., "A Simple Method for Human Peripheral Blood Monocyte Isolation," Mem Inst Oswaldo Cruz, vol. 95, No. 2, Mar./Apr. 2000, p. 221-223.

Anderson, N., et al., "An Introduction to Particle Separations in Zonal Centrifuges", National Cancer Institute Monograph, No. 21, 1966, p. 9-39.

Bertram, T.A., et al., "Morphometry of Equine Neutrophils Isolated at Different Temperatures", Vet Pathol, vol. 19, 1982, p. 534-543.

Lawrence, J., et al., "Purification of Viruses by Centrifugation", Manual of Aquatic Viral Ecology, Chapter 17, 2010, p. 166-181.

"Harvesting Gradients", Application Sheet S52, Second Edition, Jan. 2009, p. 1-6.

Anderson, N.G., et al., "Preparative Zonal Centrifugation", Methods of Biochemical Analysis, vol. XV, Interscience Publishers, New York, (1967), 271-311.

Bondoc, Jr., L.L., et al., "Size Distribution Analysis of Recombinant Adenovirus Using Disc Centrifugation", J. Ind. Microbiol. Biotechnol, 20, (1998), 317-322.

Gianello, R., et al., "Isolation of Intestinal Cell Peroxisomes by Rate-Dependent Banding in a Vertical Rotor", Biochem. Mol. Biol. Int., 30(3), (Jul. 1993), 505-15.

Herr, J.K., et al., "Aptamer-Conjugation Nanoparticles for Selective Collection and Detection of Cancer Cells", Anal. Chem., 78(9), (2006), 2918-2924.

Kassab, J.R., et al., "Fast 'Hyperlayer' Separation Development in Sedimentation Field Flow Fractionation", J. Chromatogr. B, 826, (2005), 8-16.

Marziali, A., et al., "An Arrayable Flow-Through Microcentrifuge for High-Throughput Instrumentation", Proc. Natl. Acad. Sci. USA, 96, (1999), 61-66.

Menys, V.C., et al., "Isolation of Plasma Small-Dense Low-Density Lipoprotein Apolipoprotein B", Clin. Chem. Lab. Med., 42(1), (2004), 30-36.

Norina, S.B., et al., "Image Analysis of Bioparticles Accumulation and Diamagnetic Alignment in High-Gradient Magnetic Field", J. Biomed. Opt, 10(5), (Sep.-Oct. 2005), 051702.

Pafko, W., "Centrifuge Settling & Filtration Theory", Centrifuge Settling & Filtration Theory, Chapter XII, Special Topics Report at www.pafko.com/wayne/docs/centrifuge.pdf, pp. 1-6.

Potts, J.L., et al., "Separation of Lipoprotein Fraction by Ultracentrifugation: Investigation of Analytical Recovery with Sequential Flotation and Density Gradient Procedures", Clin. Chim. Acta., 230(2), (Oct. 31, 1994), 215-20.

Pretlow, II, T.G. et al "Velocity Sedimentation of Organelles at Low Centrifugal Force in an Isokinetic Gradient", Biochem. J., (1978), 174: 303-307.

Sahoo, S.K., et al., "Nanotech Approaches to Drug Delivery and Imaging", Drug Discovery Today, 8(24), (2003), 1112-1120.

Schumaker, V.N., et al., "Sequential Flotation Ultracentrifugation", Methods Enzymol., 128, (1986), 155-70.

Snoswell, M.A., et al., "Sizing Biological Samples by Photosedimentation Techniques", Biotechnol. Prog., 6, (1990), m255-261.

Young, B.D., et al., "The Calculation of Sedimentation Coefficients in Vertical Rotors", J. Biochem. Biophys. Meth., 5, (1981), 95-104.

Havel, et al., "the Distribution and Chemical Composition of Ultracentrifugally Separated Lipoproteins in Human Serum", Sep. 1955, 1345-1353.

Brousseau, et al., "Sequential Ultracentrifugation Micromethod for Separation of Serum Lipoproteins and Assays of Lipids, Apolipoproteins, and Lipoprotein Particles", 1993, Journal of Clinical Chemistry, vol. 39, No. 6, 960-964.

U.S. Appl. No. 11/441,934 (US 2007-0272612)—Restriction Requirement—May 20, 2009.

U.S. Appl. No. 11/441,934 (US 2007-0272612)—Response/Restriction Requirement—Jun. 23, 2009.

U.S. Appl. No. 11/441,934 (US 2007-0272612)—Non-Final Rejection—Sep. 3, 2009.

U.S. Appl. No. 11/441,934 (US 2007-0272612)—Response/Amendment—Feb. 12, 2010.

U.S. Appl. No. 11/441,934 (US 2007-0272612)—Final Rejection—Apr. 26, 2010.

U.S. Appl. No. 11/441,934 (US 2007-0272612)—Response/Amendment—Oct. 26, 2010.

U.S. Appl. No. 11/441,934 (US 2007-0272612)—Advisory Action—Nov. 1, 2010.

U.S. Appl. No. 11/441,934 (US 2007-0272612)—Response/Amendment—Dec. 23, 2010.

U.S. Appl. No. 11/1441,934 (US 2007-0272612)—Non-Final Rejection—Mar. 16, 2011.

U.S. Appl. No. 11/441,934 (US 2007-0272612)—Response/Amendment—Jun. 8, 2011.

U.S. Appl. No. 11/441,934 (US 2007-0272612)—Final Rejection—Sep. 27, 2011.

Carlson, K., "Lipoprotein Fractionation"; J. clin. Path., 26, suppl. (Ass. Clin. Path.), 5, p. 32-37.

Sniegoski, L., et al., "Determination of Serum and Blood Densities", Analytical Chemistry, vol. 51, No. 9, Aug. 1979, p. 1577-1578.

Jensen, G., et al., "Determination of Background Serum Density for Lipoprotein Ultracentrifugation", Lipids, vol. 11, No. 10, Apr., 1978, p. 752-754.

* cited by examiner

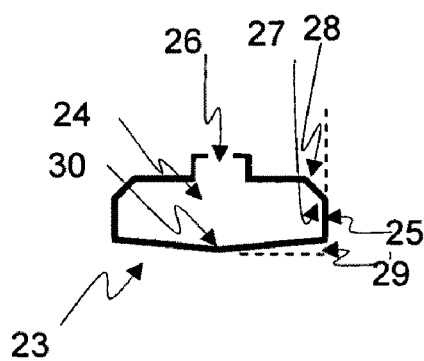
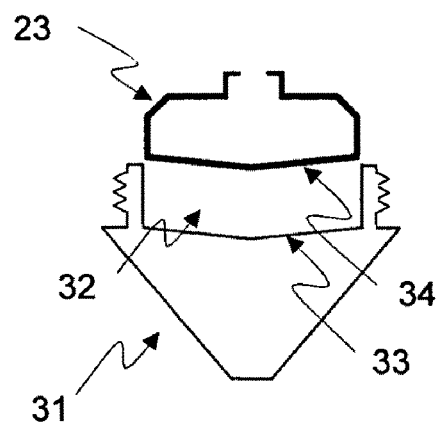
Fig. 2
Fig. 2a
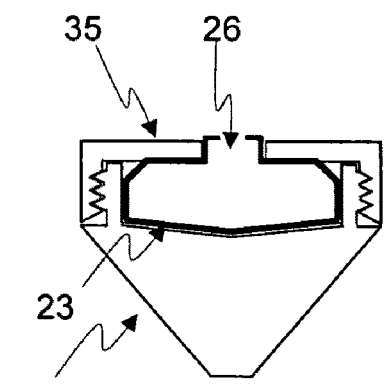
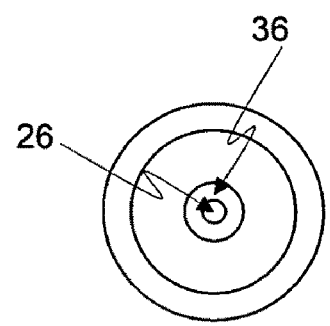
Fig. 2b
Fig. 2c

| Fraction # | Sucrose % (w/v) | Protein Conc. (mg/ml) |
|---|---|---|
| 1 | 8.5 | 8.45 |
| 2 | 10 | 5.93 |
| 3 | 14 | 3.22 |
| 4 | 18 | 1.71 |
| 5 | 22 | 1.43 |
| 6 | 26 | 1.34 |
| 7 | 30 | 1.85 |
| 8 | 34 | 2.45 |
| 9 | 38 | 3.08 |
| 10 | 42 | 3.39 |
| 11 | 46 | 2.43 |
| 12 | 50 | 1.65 |
| 13 | 54 | 0.35 |
| 14 | 60 | 0 |
| PNS | 8.5 | 22.84 |

Fig. 5

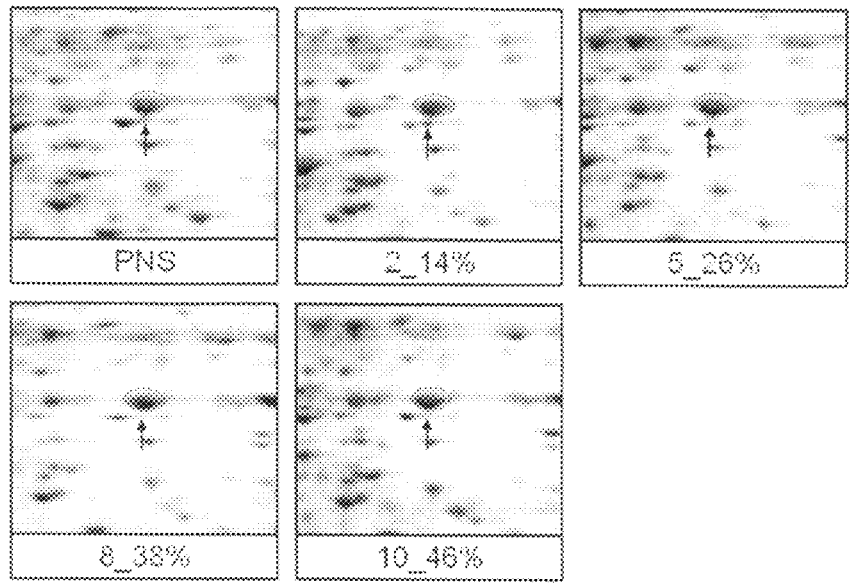
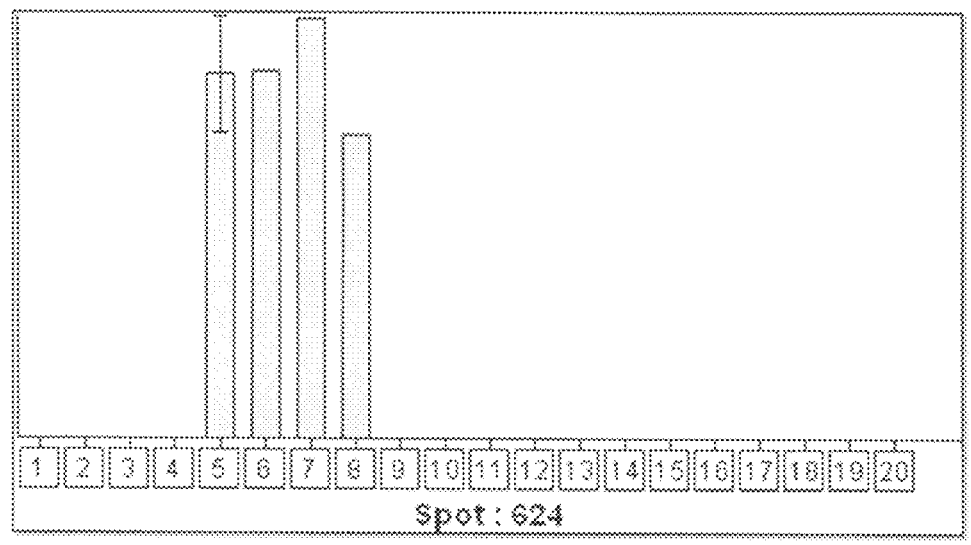
Fig. 6

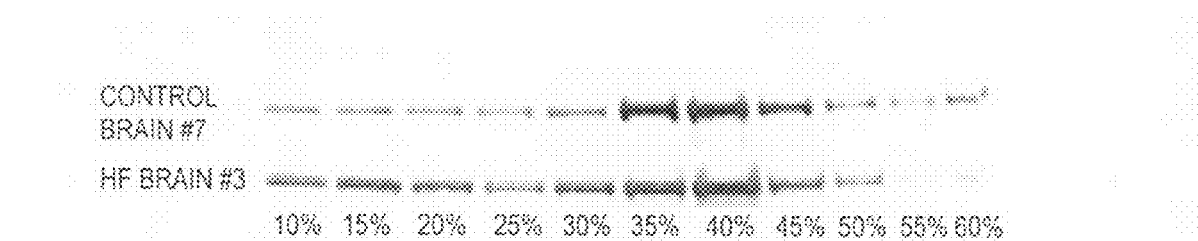
WESTERN BLOT OF P-SYNAPSIN I FROM EDGE FRACTIONED RAT BRAINS. ONE SAMPLE EACH OF A CONTROL AND A HF DIET RAT BRAIN IS SHOWN.
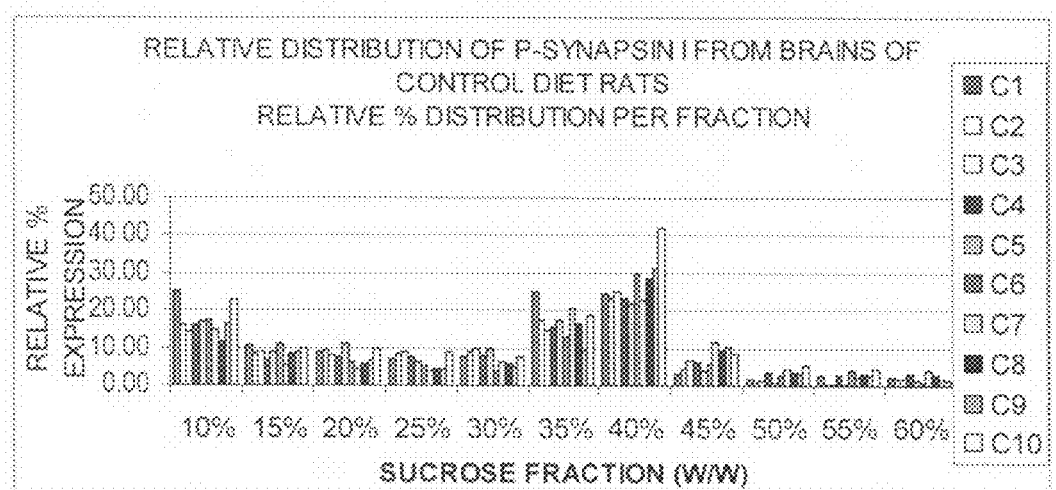
A
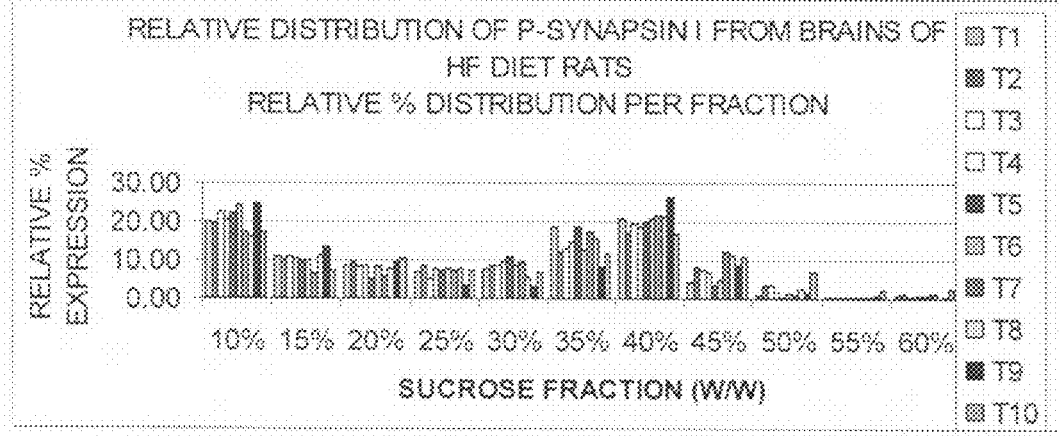
B
WESTERN BLOT ANALYSIS OF P-SYNAPSIN I FROM FRACTIONATED RAT BRAIN SAMPLES. A: RELATIVE DISTRIBUTIONS OF P-SYNAPSIN I WITHIN FRACTIONS OF CONTROL BRAINS. B: RELATIVE DISTRIBUTIONS OF P-SYNAPSIN I WITHIN FRACTIONS OF HF DIET BRAINS.
Fig. 9

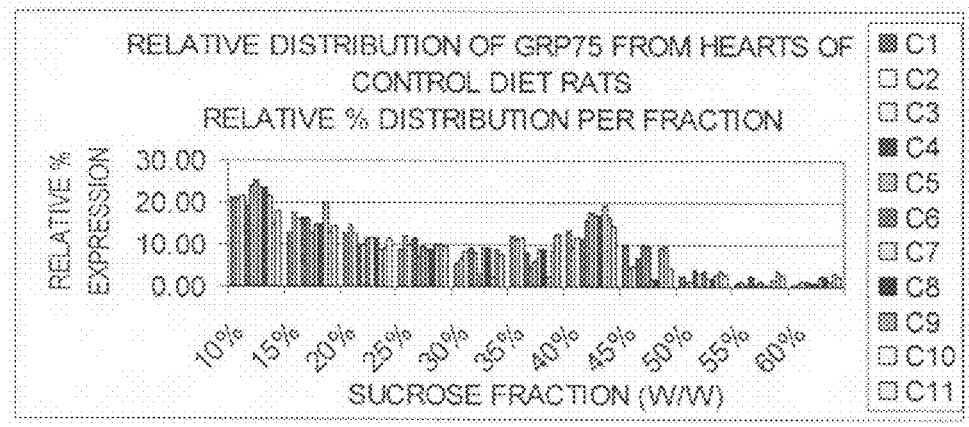
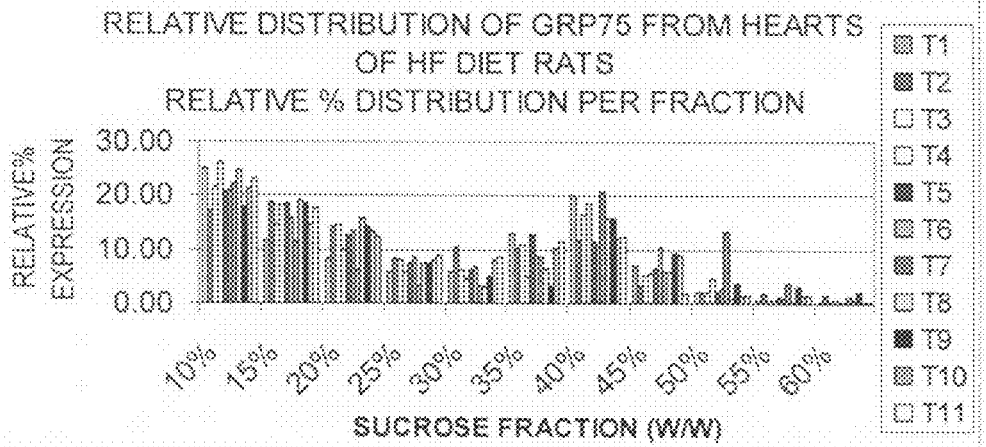
Fig. 10

Western blot analysis of prostate biopsy samples: Cancer patients, CW and RB; benign patient, JP and PM.

| | RATIO OF P-SYNAPSIN I EXPRESSION IN FRX 10% VS. FRX 40% | | | | | | | | | MEAN | SD |
|---|---|---|---|---|---|---|---|---|---|---|---|
| CONTROL | 1.01 | 0.68 | 0.58 | 0.69 | 0.78 | 0.58 | 0.64 | 0.41 | 0.52 | 0.54 | 0.64 | 0.165 |
| HF | 0.96 | 1.15 | 1.16 | 1.10 | 1.13 | 1.15 | 0.80 | 0.79 | 1.03 | 0.93 | 1.02 | 0.144 |

Graphical representation of data above. Error bars indicate mean +/- 1 SD.

METHOD FOR THE FRACTIONATION AND SEPARATION OF PARTICLES BY STEP-WISE GRADIENT DENSITY EXTRACTION

CROSS-REFERENCE TO RELATED APPLICATION

This application is a continuation-in-part of U.S. patent application Ser. No. 11/441,934, filed May 26, 2006, the disclosure of which is hereby incorporated by reference in its entirety.

FIELD OF THE INVENTION

The present invention relates to a method for the fractionation of particles, including biological particles, such as cellular compartments, cellular and subcellular particles, viruses, microorganisms, inclusion bodies, organelles from cell or tissue homogenates, organelles from cell lysates, lipoproteins and nano-particles, and non-biological particles such as micro-polymer particles (collectively "particles"), by the use of step-wise density gradient extraction, where said particles may be derived through recombinant or non-recombinant processes. Through an iterative series of substantially consecutive extractive steps, in which the density of the medium used to extract the particles is incrementally adjusted, the method described herein and variants thereof may be used to fractionate substantially well defined samples of particles from any source, including biological, chemical, or otherwise, on an analytical to a preparative scale.

BACKGROUND OF THE INVENTION

The efficient fractionation of biological particles from cell or tissue lysates or homogenates is crucial to the development of structural biology as a tool in applied proteomic and genomic technology. Subsequent identification and characterization of the particles recovered via fractionation may be facilitated by the method described herein. For example, the fractionation and enrichment of low abundance proteins from organelles is central to biomarker discovery in pharmaceutical drug development. Due to the heterogeneity of organellar particles, methods for isolation and characterization of functional low-abundance proteins specific to organellar compartments currently are very expensive, complex and time-consuming. Typically, standard methods for isolation of organelles involve multi-step centrifugations, including differential and density gradient ultracentrifugation, or electrophoretic separations. These methods usually require 24 to 48 hours to obtain acceptable separations. Furthermore, these classical fractionation methods have not kept pace with the increased sensitivity in protein analysis. The ability to supply a desired biological particles or organelles quickly and efficiently using the method described herein meets an unmet pharmaceutical and biomedical need for the identification of diagnostic markers in disease processes. Consequently, the need for an efficient, reproducible, and scalable method for the fractionation of biological particles has grown and will continue to proliferate as structural biology reveals new target proteins and organelles as points of possible intervention in the treatment of human disease processes.

Separation and purification of nano- and micro-particles are essential for any technical applications in numerous industrial fields including drug development, drug delivery, biosensors, coatings, and pigments. In recent research, aptamer-modified magnetic nano-particles and fluorescent nano-particles were demonstrated to have potential applications for cancer and other medical diagnostics (Herr, J. K. et al, Anal. Chem. 2006, 78(9), 2918-2924). Significant advantages have been shown in using bioconjugated nanoparticles for biosensing and bioimaging, such as cell staining, DNA detection and separation, rapid single bacterium detection, and biotechnological application in DNA protection. (Sahoo, S. K. and Labhasetwar V., Drug Discov Today. Dec. 15, 2003; (24): 1112-20) Fractionation and separation of these nanoparticles to generate defined or uniform particles prior to or after applications can benefit from the method described herein.

Separation of particles can be accomplished by simple gravity sedimentation. In this procedure, the samples are allowed to sit and separation occurs due to the differences in the size and shape of the particles. Gravitational sedimentation has limited practical value for particles under a few micrometers in diameter due to the prohibitively long settling times. The sedimentation process can be accelerated by coupling driving forces including centrifugal force, magnetic force, electric force and other forces.

The most common methods to separate particles have involved the use of centrifugation including, differential, rate-zonal and isopycnic centrifugation. Overall the velocity of sedimentation of particles in a centrifugal field is described by the Stokes' equation:

$$v = \frac{d^2(\rho_p - \rho_1)}{18\eta} g$$

where
$v$=sedimentation velocity
$d$=diameter of particle
$\rho_1$=density of medium
$\rho_p$=density of particle
$g$=gravitational field (RCF)
$\eta$=viscosity of medium This velocity, the sedimentation velocity, is determined by the size, density and shape of the particle, as well as the viscosity of the medium through which it must travel and the centrifugal force generated.

In differential centrifugation, the suspension of particles in a medium is placed in a centrifuge tube and centrifuged for a specific period of time using a specific relative centrifugal force (RCF) to separate the group of largest particles. Then the supernatant is removed from the pellet into a separate tube, and recentrifuged for another specific period of time with another specific RCF to collect the group of the next largest particles. A series of pellets are obtained by the application of incremental increases in the RCF and time. In this process, the density of the medium is kept constant, particles are separated by changing centrifugal time and RCF, and the collected pellets are the resulting fractions of the separation. Obtaining a stable pellet using differential centrifugation depends upon the RCF, sedimentation velocity, and distance the cellular particle has to travel. The longer a sample is subjected to a specific RCF, the more likely the pellet will become contaminated by smaller particles intermixed with larger particles. The long sedimentation pathway between, and the difference in the RCF between the top and the bottom of the sample are primarily responsible for the lack of resolution and poor recoveries associated with the use of differential centrifugation. Differential centrifugation is an effective method at separation of particles into broad size classes but not suitable for separation of particles of similar sizes.

A method that results in greater resolution than differential centrifugation of all particle sizes is rate zonal gradient centrifugation. Practically, this is achieved by layering a suspension of particles on top of a preformed density gradient and then subjecting the sample to a specific RCF. Each particle size will migrate as a zone or band at a characteristic velocity. In this method, the density of the particles is always greater than the density of the liquid. In a continuous gradient, the density increases in a linear or non-linear fashion. By allowing the particles to sediment through such a density gradient, the resolution of particles is generally improved. The particles move down through the gradient in the form of discrete zones at a rate that depends primarily on their size. The centrifugation time needs to be tightly controlled—just long enough to separate the particles of interest. If the centrifugation time is too short, the particles will not separate sufficiently. If the centrifugation time is too long, some or all of the particles will end up in a pellet at the bottom of the tube. Another important limitation of using this method is that the volume of the sample is typically no more than about 5% by volume of the total volume of the density gradient used in the separation. Band broadening occurs when the capacity of the gradient is exceeded. A concentrated band of sedimentation particles can raise the density of the sample zone above that of the gradient immediately below it, leading to instability and band broadening.

Another commonly used centrifugation method for separation of particles is isopycnic centrifugation, which is also called equilibrium density gradient centrifugation. In this process, particles are either layered onto a gradient or dispensed throughout the gradient. Under centrifugal force, particles separate based on their buoyant densities, i.e., the particles migrate to a position within the gradient where their densities equal the density of the surrounding medium, called their isopycnic position. The advantage of isopycnic centrifugation over rate zonal density centrifugation is that the particles accumulate at their own equilibrium densities within the gradient as a result of the centrifugal force and the counteracting buoyant density of the gradient. Unlike rate zonal centrifugation, the sample volume may be as large as 80% of the total liquid volume. However, the resulting sample separation is distributed throughout the total fluid volume. Since it will take an infinite time to reach true equilibrium, the biggest limitation of isopycnic centrifugation is the damage to biological particles, particularly organelles, which is much greater than other methods. Because the centrifugation times are much longer, particles are exposed to potential damage or decomposition by both centrifugal force and high density gradients for extended periods of time. Additionally, long gradient columns may result in hydrostatic pressures sufficient to damage cell organelles.

Both rate zonal and isopycnic density centrifugation methods require the use of a density gradient medium for centrifugation to ensure stable sedimentation. Density gradients for isopycnic centrifugation can be either continuous, such as linear, convex, or discontinuous, while continuous density gradients are required for rate zonal centrifugation. Preparation of density gradients requires a certain level of skill in the art. Generally, density gradients can be prepared by using either a diffusion method, which requires up to 24 hours to form the gradient, or a gradient mixer. However, the shape and steepness of the gradient depends on the type of medium and the centrifugal force as well as the type of rotor used. Hence, it is difficult to ensure that the correct shape of the gradient is obtained. Another major disadvantage of both rate zonal and isopycnic density gradient centrifugation is defining the exact density of resulting fractions. Special instruments, such as refractometers, pycnometers and density meters, as well as calculations are required to determine the density of each resulting fraction.

Another commonly used method for the specific separation of lipoprotein particles is sequential flotation ultracentrifugation (Potts, J. L. et al., Clin Chim Acta, 1994, 230 (2), 215-220). In this process, the density of lipoprotein-containing liquid samples, such as plasma or serum, is adjusted by addition of solid salts, such as sodium chloride or sodium bromide, and subjected to ultracentrifugation. The top of the supernatant is removed, either by cutting off the upper portion of the centrifuge tube or by pipetting. Heavier lipoprotein particles are obtained by increasing the density of the remaining liquid sample by the further addition of solid salt, and further ultracentrifugation. Each ultracentrifugation step generally requires 20-40 hours. In addition to the disadvantage of lengthy process times, the sequential removal of substantial amounts of sample at each step and the need for the addition of solid salt significantly limits the utility of this method.

Magnetism is another force that can be used for the separation of particles. An applied magnetic field acting on micrometer and submicrometer particles having diamagnetic or paramagnetic susceptibility causes their movement. This process has been used in pigment production, nanomagnetics production for electronics and in bio-separation. Although the applied magnetic field can possibly exceed the centrifugal force, it has not been used to accelerate particle sedimentation.

Particles can also be separated by electrophoresis, a method which can separate particles based on their inherent charge and size and their subsequent migration in an applied electric field. For example, organelles are charged at neutral pH due to the presence of acidic and basic groups on their surface and will migrate in an applied electric field. The rate of movement is proportional to the charge and inversely proportional to the viscous drag, hence the rate of movement is strongly influenced by particle size. A limitation of this method is stabilizing the migrating zone of particles. Also, uneven heating of the liquid is generated by the electric current. Moreover, most of the major organelles appear to have rather similar electrophoretic mobility and it is often necessary to resort to modification of the surface charge enzymatically before a satisfactory separation can be achieved.

The instant method does not require the use of density gradients to separate particles. The separation media used are solutions of a specific density which can be incrementally adjusted during the practice of the method. The separation of particles is based on a step-wise gradient extraction of particles based on their density. The method of the invention relies upon the difference in density between subsets of particles in the sample and that of the extracting medium. Based on the Stokes' equation, particles that are equal to or lower in density than the density of the extracting medium will not pellet in the medium. Practically, these particles will float in the extracting medium while particles higher in density than the density of the medium will sediment towards the bottom of the extracting medium and form a pellet during centrifugation. The suspended particles may exist as a colloidal or polymeric mixture. Thus, the surface of the extracting medium is essentially a density barrier preventing the sedimentation of particles that are less dense than or equally as dense as the extracting medium. In this manner, the supernatant containing particles with a density less than or equal to the density of the extracting medium ($\rho_1^1$) can be isolated. The remaining pellet can then be resuspended in an extracting medium where the density has been increased incrementally ($\rho_1^2$) and then centrifuged at a specific speed over a specific period of time resulting in a supernatant containing particles that have a density in the range greater than $(\rho_1^{\ 1})$ and less than or equal to $(\rho_1^{\ 2})$.

The remaining pellet can then be optionally treated iteratively by the above method to obtain additional particles present in a sample depending upon their density. This iterative treatment may be optionally repeated until a desired density of the medium is reached or until no pellet is produced via centrifugation. Thus, the method demonstrates a stepwise extraction of particles from a pellet of a sample which is capable of differentiating substantially all the particles inherent to a particular sample via their density without the use of any type of density gradient currently used in most, if not all, centrifugal fractionations of particles.

The design of the centrifuge and the type rotor(s) employed to practice the above described method varies but the most common suitable design is based on a horizontally rotatable hollow disk driven by an air compressor which can be set to run at a wide variety of speeds to enable the fractionation of a wide variety of particles. Prepared samples can be loaded into the center of the horizontally rotatable hollow disk, at rest or in motion, at the start of the analysis. The rotation of the disk carries the various particles of the samples either to the surface of, or to within the suspension of, the liquid volume of the extracting medium of specific density contained within a sedimentation chamber in the horizontally rotatable hollow disk or to the pellet formed within the sedimentation chamber. After a specific period of time, the supernatant containing the extracted particles is removed by aspiration or other means from the sedimentation chamber. A new liquid volume of extracting medium of specific density then is added to resuspend the resultant pellet formed from the initial centrifugation of the sample. The method may then be repeated as many times as desired for the particular sample being analyzed.

Accordingly, there is a significant need in proteomic and genomic technology for an efficacious method for the fractionation of particles that is scale invariant, easily automated, generic for a broad range of particles and economical. It has now been surprisingly found that the use of step-wise density gradient extraction allows the defined fractionation of a wide variety of particles under conditions which are scale invariant, easily automated, and economically feasible for analytical to preparative samples.

Biomarker discovery, evaluation, and validation are the key steps in biomarker development processes. The recent development of high-throughput proteomics has significantly increased the current database of potential biomarkers. However, very few of these biomarkers are ever found to be clinically relevant. In fact, the U.S. Food and Drug Administration ("FDA") approval rate of biomarkers has continued to decrease annually. The challenges of biomarker development continue to be the processes of evaluating and validating hundreds or thousands of these biomarker candidates to find those truly indicative of diseases with utility in prognosis or diagnosis.

While the discovery process of biomarker development produces candidates on a large scale, the evaluation and validation steps of the process remain an impediment to future development. Current bottlenecks include the lack of a system and a method which can rapidly separate candidates which are highly specific in the prognosis or diagnosis of human disease process from those with less specificity, validation steps which are slowed by the need for high sensitivity reagents, and validation processes which are expensive and time consuming.

Only five new protein markers were approved by the FDA (Chem, 2008; 54(11):1749-52). This dearth of new protein biomarkers comes on the heels of a 2004 FDA white paper calling attention to an alarming decline in the number of innovative medical products being submitted for FDA approval (Food and Drug Administration. Innovation or Stagnation: Challenges and Opportunity on the Critical Path to New Medical Products; http://www.fda.gov/oc/initiatives/criticalpath/whitepaper.html. 2004) and a March, 2006 follow-up, *Critical Path Opportunities Report and List* (http://www.fda.gov/oc/initiatives/criticalpath/reports/opp_report.pdf).

Carr and Anderson (Carr, S. A. and Anderson, L., Clin. Chem. 2008; 54 (11): 1749-52) reported that is now common for differential analyses of tissue or plasma samples to confidently identify thousands of proteins, hundreds of which can vary in concentration by five-fold or more between control and diseased/treated samples. These proteins are found to be differentially expressed between the normal and diseased states based on semiquantitative assessment of relative protein or peptide abundance using 2D gel electrophoresis, mass spectroscopic data or exogenous isotopic labeling. Some of these candidates will be false positives—proteins that upon further evaluation are not truly differentially expressed within the parameters of interest. The false positive discovery rate is expected to be high, particularly for low-abundance proteins, giving rise to the term "candidate biomarkers, as opposed to biomarkers. "Distillation of true positives from the total pool of candidates is the single greatest challenge in biomarker development, and is the emphasis of most phases of the biomarker pipeline" (Rifai et al, *Nat. Biotechnol.* 2006, 24, 971-983.).

Studies involving lower abundance proteins typically rely on multidimensional fractionation, at times leading to 100 subfractions, each requiring lengthy analysis. In many cases, analysis of a single case/control sample pair can involve up to 2 weeks of instrumentation time, severely limiting the number of statistically relevant comparisons that may be run. As such, perhaps as many as 95% of the protein biomarkers discovered in these experiments are false positives, arising solely from biological or technical variability (Carr and Anderson, 2008).

ELISA is an assay used for both verification and clinical validation of biomarkers, having relatively high throughput and extraordinary sensitivity for quantifying the target analyte. ELISA development, however, is costly ($100 000-$2 million per biomarker candidate), has a long development lead time (>1 year) and a high failure rate. As such, development of ELISA assays for all potential biomarkers is highly impractical, with only a few percent of all to be used as the ultimate validation of biomarkers, there is a need for "affordable bridging technologies to facilitate testing of a large number of potential candidates" (Paulovich, A. G., et al., Proteomics Clin. Appl. 2008; 2: 1386-1402).

What is required for most candidate biomarkers, according to Carr and Anderson (2008), is an intermediate verification technology having, among other things, shorter assay-development time lines, lower assay costs, low sample consumption, and a high-throughput, good precision analytical capability. Such a verification approach could potentially identify from an initial list of hundreds of candidate protein biomarkers those few that are worth advancing to higher level validation studies.

Accordingly, there is a significant need in biomarker evaluation and validation to establish a method that is accurate, reliable, rapid and cost effective for the determination of those biomarker candidates which are truly indicative of diseases with utility in prognosis or diagnosis. It has now been surprisingly found that the use of step-wise density gradient extraction combined with a novel statistical analysis allows a quick and cost effective evaluation of potential biomarkers by comparing the observed ratio of a potential biomarker from different gradient fractions of a negative control tissue or cell sample lysate with the observed ratio for the potential biomarker, using the same gradient fractions as the negative control, from a positive control tissue or cell sample lysate.

The identification of biomarkers is an essential element for the early prediction of diseases and is central to the emerging field of translational (or personalized) medicine. The presence and identification of biomarkers for human diseases at an early stage of a disease may allow for early intervention and successful treatment. Likewise, the efficacy of various treatments (surgical and non-surgical) may be increased with a concomitant increase in survival rates from diseases such as the many forms of cancer, heart disease, and neurodegenerative diseases such as Alzheimer's disease. By using the instant method, compounds characterized as biomarkers may be readily obtained.

Pathologic analyses of cancer biopsies are performed by a variety of methods. The objective of this type of analysis is usually to determine the sensitivity, accuracy, and clinical relevance of the technique in cancer management. Correct identification and removal of metastatic disease during surgery may prevent the need for a second surgery. Currently, the majority of pathologic analyses are performed post-surgery, leaving open the possibility that elements of the metastatic disease may not be totally removed during surgery. Accordingly, there is a substantial need to develop accurate intraoperative procedures to differentiate between healthy (negative margin) and diseased (positive margin) tissue.

Breast cancer is the most frequently diagnosed malignancy in women. Breast conserving therapy (BCT) along with radiotherapy has become the standard of treatment for most breast tumors. The choice of BCT is based upon the ability to achieve a pathological negative margin of resection. The presence of a positive margin indicates the need for further surgery to achieve negative margins. Patients undergoing BCT carry a permanent risk of local recurrence, with positive margin being the strongest predictor. Microscopic residual disease at margins accounts for up to 25% of recurrence 3 to 5 years after BCT while a maximum of 5% recurrence exists for negative margin patients. (Karni, T., et al., The American Journal of Surgery 194; 2007; 467-473).

In an optimal case, clear margins should be obtained within the first surgical procedure. However, repeated surgical procedures are often required for conversion of patients to negative margin status. Re-excision rates vary widely as there is no consensus on the required clear margin width. Because excision of unnecessarily large-tissue volumes negatively impacts cosmetic results, a reliable method is necessary for optimized assessment of the excision intraoperatively. Such a method will help to balance the risk of local recurrence, multiple re-excisions and associated psychological issues, costs, and acceptable cosmetic outcome. Thus, the availability of intraoperative margin assessment data combined with postoperative pathological data may improve patient management.

An intraoperative margin-assessment device has been used by breast surgeons. The device is based on radiofrequency spectroscopy, measuring and quantifying the variable electromagnetic response of malignant and normal cell types under an array of frequencies. This process enables the user to compare the reflected signal to a preacquired library of signals and a classification as "positive" or "negative". The device includes a console and a disposable probe which is sensitive to malignant tissue at the resected specimen surface up to a depth of 0.1 cm. The device has been used to determine margins in an intraoperative manner by comparing the device readings to histological analysis on individual measurement points and their affiliated margins. However, device detection ability decreases with the increase in margin depth and that to be successful, all positive margins in a patient must be detected by the device. (Id. at 472).

The most common intraoperative procedure for pathological diagnosis has been the preparation of a frozen section (FS) of the affected area. Indications for FS include making a diagnosis, evaluating margin status, determining tumor extent/spread, and obtaining an adequate sample for diagnosis. FS provides real-time evaluation usually within 20 minutes. This process includes gathering clinical and radiological information, utilizing rapid methods for tissue sampling, preparing slides, staining, performing microscopic examination, and ultimately making a diagnosis. Despite the high degree of accuracy of FS, there are limitations to its use. Frozen artifact can produce inferior slides for microscopic evaluation and sampling errors can result from the heterogeneity of a tumor. (Bui, M. M. et al., Cancer Control, 2008, 15 (1), 7-12). Also, accurate analysis of micrometastases at the molecular level is not possible with the use of optical microscopy.

There are no consensus guidelines for the diagnostic approach to biopsy a bone or soft tissue tumor. Core biopsy is the most common approach while other methods such as FS, image-guided biopsy, and fine needle aspiration biopsy have been used to evaluate musculoskeletal sarcomas and tumors. Notably, there are no standard protocols for the intraoperative FS preparation of bone and soft tissue tumors. For these type of tumors, an interdisciplinary approach was necessary to correlate clinical, radiological, and pathological information to reach an intraoperative diagnosis (Id. at 12).

In breast cancer the status of axillary lymph nodes is one of the most important factors in predicting long-term survival and in determining the need for adjuvant therapy in breast cancer. Axillary lymph node dissection (ALND) is the most common procedure to detect lymph node metastasis and is therapeutically useful for the regional control of axillary metastases. However, this surgical method is associated with significant long-term morbidity. Sentinel lymph node (SLN) biopsy is an alternative method for the assessment of lymph node status in patients with morbidity markedly less than ALND. The ultimate goal of this procedure is to spare the patient a second surgery.

While this diagnostic method is considered accurate and reliable, the use of SLN frozen sections for intraoperative diagnosis is controversial because the results are highly variable. (Leung, K. M., et al., Hong Kong Med J, 2007, 13(1), 8-11). The overall results of intraoperative examination indicated that both the SLN positive rate and FS sensitivity increased with the size of the tumor. However, a common observation from this technique was that the false-negative rate is higher among patients with small tumors. This was reportedly due to a higher proportion of micrometastasis in such patients. (Weiser, M. R. et al., Ann Surg Oncol, 2000; 7:651-5; Wada, N., et al., Jpn J Clin Oncol; 2004; 34(3) 113-117). Therefore, the sensitivity of intraoperative examination of SLN in breast carcinoma is tumor size dependent, and false-negative results were largely due to failure to detect micrometastasis.

Accordingly, there is a significant need in the clinical management of patients suffering from cancer and other diseases to establish a method that is accurate, reliable, rapid and cost effective for the determination of positive margins intraoperatively. It has now been surprisingly found that the use of step-wise density gradient extraction allows the rapid and accurate assessment of positive margins intraoperatively by comparing observed ratios of predetermined biomarkers from different gradient fractions of the test tissue sample lysates with defined ratios for the predetermined biomarkers which are determined by using the same gradient fractions as the test tissue sample lysates and obtained from negative and positive margins of control tissue samples from an individual patient.

SUMMARY OF THE INVENTION

Thus, it is an object of this invention to use a step-wise gradient density extraction of a mixture of particles by varying the density of the extracting medium to obtain particles of discrete density from the sample. The results obtained are analogous to those using a density gradient without the problems inherent in density gradient sedimentation.

It is a further object of this invention to provide a step-wise method whereby samples containing a wide variety of particles of differing densities may be efficiently fractionated by collecting those particles remaining suspended in a liquid volume of an extracting medium from each step and resuspending the resultant deposit in an extracting medium of different density ($\rho_1^2$) than the density of the initial extracting medium ($\rho_1^1$). Thus, if the density $\rho_1^2$ is greater than the density $\rho_1^1$, the extracted particles will necessarily have a density greater than ($\rho_1^1$) but less than or equal to ($\rho_1^2$). Essentially, the particles obtained in this manner will have a net buoyancy in the extracting medium.

It is a further object of this invention to provide a method to separate particles of different densities where the density difference is at least about 0.0001 grams/cm³ about 0.2 grams/cm³.

It is a further object of the invention to provide a method wherein the density-based step-wise extraction of particles continues in an iterative fashion until all particles have been extracted.

It is still further an object of the invention to increase the density of the extracting medium in increments of about 0.0001 grams/cm³ to about 0.2 grams/cm³ when the method is performed in an iterative fashion.

It is a further object of the invention to separate the particles of the sample in a sedimentation chamber of a horizontally rotatable hollow disk, in a manner that allows the suspension of particles to be removed from the deposited particles.

It is a further object of the invention to separate the particles of the sample within a sedimentation chamber of a removable receptacle within a horizontally rotatable hollow disk in a manner that allows the suspension of particles to be removed from the deposited particles.

It is a further object of the invention to separate the particles of the sample in a sedimentation chamber of a horizontally rotatable hollow disk designed in such a manner that allows the more dense particles to move through a very short path length within the liquid volume of the extracting medium before forming a deposit in the removable receptacle.

It is a further object of the invention to separate the particles of the sample within a sedimentation chamber of a removable receptacle in a horizontally rotatable hollow disk designed in such a manner that allows the more dense particles to move through a very short path length within the liquid volume of the extracting medium before forming a deposit in the removable receptacle.

It is a further object of the invention to provide a sedimentation chamber of a horizontally rotatable hollow disk, or a sedimentation chamber of a removable receptacle in a horizontally rotatable hollow disk, with a conically concave bottom side, wherein the bottom side rises from a bottom vertex at the center of the bottom side, at an angle of about 1 to about 10 degrees from the horizontal plane, to meet the vertical sides of the chamber, in such a manner as to allow the suspension of particles to be nearly totally removed from the chamber.

It is a further object of the invention to provide a sedimentation chamber of a horizontally rotatable hollow disk, or a sedimentation chamber of a removable receptacle in a horizontally rotatable hollow disk, with an inward taper, which taper joins the top of the vertical wall of the chamber with the horizontal top of the chamber at an angle of about 25 to about 65 degrees from the vertical plane, in such a manner as to prevent the deposited particles from forming a large, difficult to suspend particle mass at the internal intersection of the vertical wall and the horizontal top of the chamber.

It is a further object of this invention where the extracting medium of specific density is an aqueous solution, a non-aqueous solution, or any mixture of a non-aqueous and aqueous solution.

It is a further object of this invention to provide a method for separating particles of different densities from cell lysates or homogenates which originate from mammalian, plant, bacterial, yeast, or fungal cells.

It is a further object of the invention to separate particles of different densities by the application of a force to the particles, where the force applied may be centrifugal, magnetic, electrical, or mechanical.

It is a further object of the invention to separate particles consisting essentially of biological particles, proteins, nucleic acids, phospholipids, lipopolysaccharides, polysaccharides, pharmaceutically active drug substances and metabolites thereof, cellular compartments, cellular and subcellular particles, viruses, microorganisms, inclusion bodies, organelles from cell or tissue homogenates, organelles from cell lysates, protein-protein complexes, lipoproteins and nano-particles, and non-biological particles such as micropolymer particles and paramagnetic latex particles.

It is a further object of this invention to provide a method wherein the step-wise gradient density extraction of particles from a mixture of particles is based upon varying the density of the extracting medium while maintaining constant the time and centrifugal force applied at each step.

It is still a further object of this invention that the time the sample is subjected to centrifugal force is between about 1 minute to about 2 hours and the centrifugal force applied is between about 500 to 200,000 g.

It is a further object of this invention to provide a method wherein the step-wise gradient density extraction of particles requires a minimum amount of time for the separation of those particles having a density less than or equal to that of the extracting medium from those particles having a density greater than that of the extracting medium.

The basic structure of the invention involves a sedimentation chamber that can be filled with a suspension of sample in an extracting medium of a specific density. The preferred extracting medium is an aqueous solution of sucrose with a specific density. Accordingly, to effect a fractionation, the sample is always suspended in an extracting medium whose density is equal to or less than some fraction of the total particles in the sample. During centrifugation, the particles that have a density greater than that of the extracting medium migrate radially to the edge of the chamber and form a pellet along the surface of the chamber at a point furthest from the center of rotation. Particles having a density less than or equal to that of the extracting medium will essentially be suspended within the fluid in the chamber generally following Stokes' equation with their net buoyancy depending on the difference of the density of the particles and the density of the extracting medium in the centrifuge.

While the preferred embodiment of this invention utilizes a conventional, horizontally rotatable hollow disk with a sedimentation chamber as a component of an ultracentrifuge, the invention is not limited to any particular instrument design and may be applied successfully to any type of centrifuge. The method is contemplated to be performed using a semi-automated or fully automated protocol. The method of this invention can separate particles with a density difference of about 0.0001 $g/cm^3$ to about 0.2 $g/cm^3$. Thus, the method described herein is capable of the high resolution separation of particles. Additionally, the method can be applied to any combination of particles and fluid where the density of some fraction of the total particles is less than or equal to the density of the extracting medium of specific density.

To implement the method of this invention, a centrifuge, such as one of the horizontally rotatable hollow disk design, or a centrifuge, such as one where a removable receptacle within a horizontally rotatable hollow disk design may be used. At the start of the analysis, a sample of particles suspended in a liquid volume of a specific density is loaded into the sedimentation chamber of the horizontally rotatable hollow disk, or into the sedimentation chamber of the removable receptacle within the horizontally rotatable hollow disk which may be rotating or at rest. A typical sample volume can be in the range of about 0.001 to about 50 milliliters. After a sample is loaded into the sedimentation chamber the following occurs: the horizontally rotatable hollow disk, or the horizontally rotatable hollow disk and the removable receptacle within the hollow disk is accelerated to a specific speed, corresponding to a specific centrifugal force, and maintained at that speed for a specific time (the "initial sedimentation time") The sedimentation of the particles generally proceeds in accordance with Stokes' law. Typical initial sedimentation times are 1 minute to 2 hours. Thereafter, the horizontally rotatable hollow disk, or the horizontally rotatable hollow disk and the removable receptacle within, is decelerated in a controlled manner until it reaches a predetermined speed, which speed may also be zero. The liquid volume of specific density is then aspirated from the sedimentation chamber and analyzed. A pellet remains in the sedimentation chamber. The pellet remaining in the sedimentation chamber is then subjected to an extraction process which proceeds as follows. The pellet is resuspended in a liquid volume of extracting medium having a specific density which is different from that of the density of the initial suspension. A typical liquid volume of extracting medium of specific density can be in the range of about 0.001 to about 50 milliliters. After the pellet is resuspended, the horizontally rotatable hollow disk, or the horizontally rotatable hollow disk and the removable receptacle within is accelerated to a specific speed, corresponding to a specific centrifugal force, and maintained at that speed for a specific time (the "sedimentation time"). The sedimentation of the particles generally proceeds in accordance with Stokes' law. Typical sedimentation times are from 1 minute to 30 minutes. Thereafter, the horizontally rotatable hollow disk, or the rotatable hollow disk and the removable receptacle within, is decelerated in a controlled manner until it reaches a predetermined speed, which speed may also be zero. The liquid volume of extracting medium of a specific density is then aspirated from the sedimentation chamber and analyzed. This extraction process can be repeated as many times as desired to obtain a profile of particles that differ in density.

It is yet a further object of this invention to use the method described herein to target a specific density difference in a sample and perform the method using only two specific densities to obtain only particles within the density range selected. The selected density difference can be at least 0.0001 $g/cm^3$ to about 0.2 $g/cm^3$.

It is a further object of this invention to provide a method for separating particles of different densities from cell lysates or tissue homogenates, so as to enable the comparison of the relative percentage protein composition, content, and amount within a fraction (X) within the first lysate or homogenate with the relative percentage protein composition, content, and amount within an identical fraction (X) of a second lysate or homogenate wherein the method for separating the first and second lysate or homogenate is identical.

It is a further object of this invention to provide a method for separating particles of different densities from cell lysates or tissues homogenates, so as to enable the comparison of absolute or relative percentage protein composition, content, and amount within a fraction (X) within the lysate or homogenate with the absolute or relative percentage protein composition, content, and amount within a fraction (Y) of the same lysate or homogenate wherein the comparison may be a ratio, graphical overlay, overlay or electrophoresis gels or other analytical data.

It is a further object of this invention to provide a method for separating particles of different densities from cell lysates or tissues homogenates, so as to enable the comparison of (1) the ratio of absolute or relative percentage protein composition, content, and amount within a fraction (X) within a lysate or homogenate (A) with the absolute or relative percentage protein composition, content, and amount within a fraction (Y) of the same lysate or homogenate (A) with (2) the ratio of absolute or relative percentage protein composition, content, and amount within a fraction (X) within a lysate or homogenate (B) with the absolute or relative percentage protein composition, content, and amount within a fraction (Y) of the same lysate or homogenate (B).

These and other objects of the invention will become apparent to one of ordinary skill in the art upon review of the specification and claims.

In accordance with the present invention, we have discovered an efficient process for the separation of particles. This process reduces the need for cumbersome steps conventionally used to produce particles of interest with a substantially defined density. Once optimized, the process is scale invariant allowing the production of analytical to preparative samples of desired particles by semi-automated or automated protocols.

BRIEF DESCRIPTION OF THE FIGURES

FIG. 1a illustrates a side cross-sectional view of a section of the components of a horizontally rotatable hollow disk assembly used to practice the method described herein.

FIG. 1b illustrates a side cross-sectional view of a section of a horizontally rotatable hollow disk assembly used to practice the method described herein.

FIG. 1c illustrates a top view of a horizontally rotatable hollow disk assembly used to practice the method described herein.

FIG. 2 illustrates a side cross-sectional view of a section of a removable receptacle used in a horizontally rotatable hollow disk used to practice the method described herein.

FIG. 2a illustrates a side cross-sectional view of a section of a removable receptacle as used in a horizontally rotatable hollow disk used to practice the method described herein.

FIG. 2b illustrates a side cross-sectional view of a section of a removable receptacle and the horizontally rotatable hollow disk assembly used to practice the method described herein.

FIG. 2c illustrates a top view of a removable receptacle and the horizontally rotatable hollow disk assembly used to practice the method described herein.

FIG. 5 illustrates the protein concentrations from fractionation steps obtained using the method of the invention.

FIG. 6 illustrates the 2D gel image of selected fractions and PNS as well as the histogram of protein spot 624 from the 2D gel image analysis.

FIG. 9 illustrates the western blot analysis and relative percentage distribution of p-synapsin I within control and High Fat diet rat brain samples.

FIG. 10 illustrates the western blot analysis and relative percentage distribution of GRP75 within control and High Fat diet rat heart samples.

DETAILED DESCRIPTION OF THE INVENTION

Figure 1:
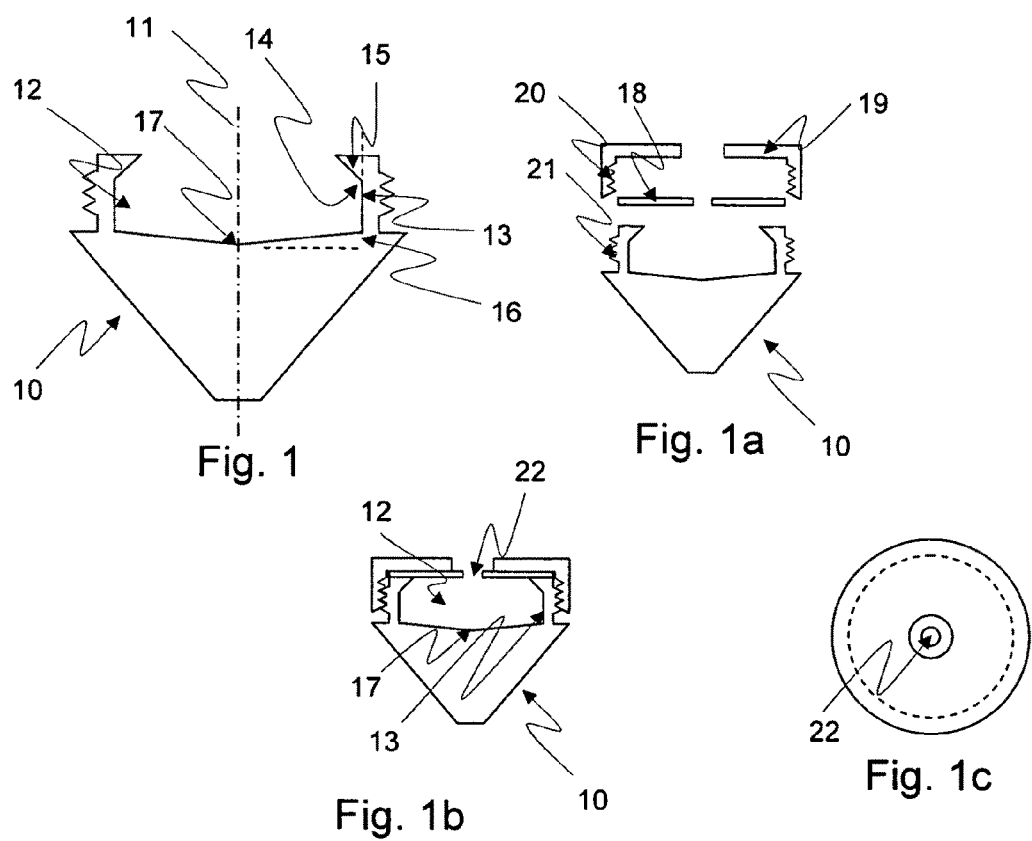
FIG. 1 illustrates a side cross-sectional view of a section of a horizontally rotatable hollow disk used to practice the method described herein.

FIG. 1. illustrates a side cross-sectional view of a section of a horizontally rotatable hollow disk 10 used to practice the method described herein. The horizontally rotatable hollow disk 10 rotates around its axis of rotation 11 and has a sedimentation chamber 12 for the fractionation of a sample containing particles. Upon the application of centrifugal force to the sample, those particles having greater density than the extracting medium will be deposited on the vertical wall 13 of the sedimentation chamber. It was surprisingly found that particles deposited in a large, tightly deposited mass, which was difficult to resuspend, at the top of the vertical wall 14 when the angle of the chamber top edge 15 was 90 degrees. It was found that as the angle 15 was made more acute, the deposited mass became easier to resuspend. As angle 15 approached 0 degrees, however, the particles rose higher on the vertical wall, adversely affecting the efficiency of the deposition. While values of about 25 to about 65 degrees for angle 15 are effective, a value of about 45 degrees is the preferred angle. When the bottom of the sedimentation chamber is flat, i.e., when angle 16 is 0 degrees, it is difficult to remove nearly all of the suspended particles from the sedimentation chamber. Increasing the angle 16 of the bottom of sedimentation chamber radially in relationship to the horizontal plane creates a conical concavity 17 at the bottom of the chamber. As angle 16 increases, however, it becomes more difficult to move the medium up the slope to the wall. Angles of about 1 to about 10 degrees provide a useful concavity, with an angle of 5 degrees being preferred. The concavity thus formed provides a suitable position from which to remove the particle suspension following the depositing of particles. Since the vertex of the concavity 17 is on the axis of rotation 11, automation of the method is facilitated by a single point of addition and removal of media.

FIG. 1a illustrates a side cross-sectional view of a section of the components of a horizontally rotatable hollow disk assembly used to practice the method described herein. The assembly includes the horizontally rotatable hollow disk 10 having external threads 21 which engage the internal threads 20 of the hollow disk cap 19. A sealing disk 18 provides a seal between the cap and the horizontally rotatable hollow disk.

FIG. 1b illustrates a side cross-sectional view of a section of a horizontally rotatable hollow disk assembly used to practice the method described herein. When the components of FIG. 1a are assembled, the horizontally rotatable hollow disk 10 becomes part of an assembly having a sedimentation chamber 12, a vertical wall 13 onto which to deposit particles, a concavity 17 from which to nearly totally remove suspended particles, and an opening 22 through which to add and remove sample.

FIG. 1c illustrates a top view of a horizontally rotatable hollow disk assembly used to practice the method described herein, and shows the opening 22 through which sample is added or removed.

At times, it may be preferable to practice the method in a removable receptacle to eliminate the need for stringent cleaning of the horizontally rotatable hollow disk between every sample fractionation. A removable receptable provides a disposable receptacle for use with every fractionation, removing the need for stringent cleaning, and providing a reproducible environment for every fractionation. The removable receptacle is preferably made of polyethylene or polypropylene. The removable receptacle embodies most of the characteristics of the horizontally rotatable hollow disk and its assembly described previously and in FIGS. 1-1c.

FIG. 2 illustrates a side cross-sectional view of a section of a removable receptacle used in a horizontally rotatable hollow disk used to practice the method described herein. The removable receptacle 23 contains a sedimentation chamber 24. Sample is loaded into the sedimentation chamber through opening 26 and particles that are more dense than the sample medium are deposited on the inside of the vertical wall 25 following application of centrifugal force to the removable receptacle when used in a horizontally rotatable hollow disk. In a manner similar to the description above, particles which deposited in a large, tightly deposited mass, at the top of the vertical wall 27 when the angle of the chamber top edge 28 was 90 degrees became easier to suspend as the angle 28 was made more acute. As angle 28 approached 0 degrees, however, the particles rose higher on the vertical wall, adversely affecting the efficiency of the deposition. While values of about 25 to about 65 degrees for 28 are effective, a value of about 45 degrees is the preferred angle. When the bottom of the sedimentation chamber is flat, i.e., when angle 29 is 0 degrees, it is difficult to remove nearly all of the suspended particles from the sedimentation chamber. Increasing the angle 29 of the bottom of sedimentation chamber radially in relationship to the horizontal plane creates a conical concavity 30 at the bottom of the chamber. As the angle increases, however, it becomes more difficult to move the medium up the slope to the wall. Angles of about 1 to about 10 degrees provide a useful concavity, with an angle of about 5 degrees being preferred. The concavity thus formed provides a suitable position from which to remove the particle suspension following the depositing of particles. Since the vertex of the concavity 30 is on the axis of rotation of the removable receptacle, automation of the method is facilitated by a single point of addition and removal of media.

FIG. 2a illustrates a side cross-sectional view of a section of a removable receptacle as used in a horizontally rotatable hollow disk used to practice the method described herein. The horizontally rotatable hollow disk 31 used with the removable receptacle 23 differs from the horizontally rotatable hollow disk of FIGS. 1-1c in that it does not contain a sedimentation chamber, and is intended the hold the removable receptable during the practice of the method described herein. The receptacle is held within a chamber 32 contained within the horizontally rotatable hollow disk 31. The contour 33 of the bottom of this chamber matches the contour 34 of the bottom of the removable receptacle.

FIG. 2b illustrates a side cross-sectional view of a section of a removable receptacle and the horizontally rotatable hollow disk assembly used to practice the method described herein. During the practice of the method described herein, the removable receptacle 23 is held in place within the horizontally rotatable hollow disk 31 by a cap 36. Sample can be added or removed through the opening 26 in the removable receptacle.

FIG. 2c illustrates a top view of a removable receptacle and the horizontally rotatable hollow disk assembly used to practice the method described herein. Sample is added through the opening 26 in the top of the removable receptacle. A portion 36 of the top of the removable receptacle protrudes through the cap.

Figure 3:
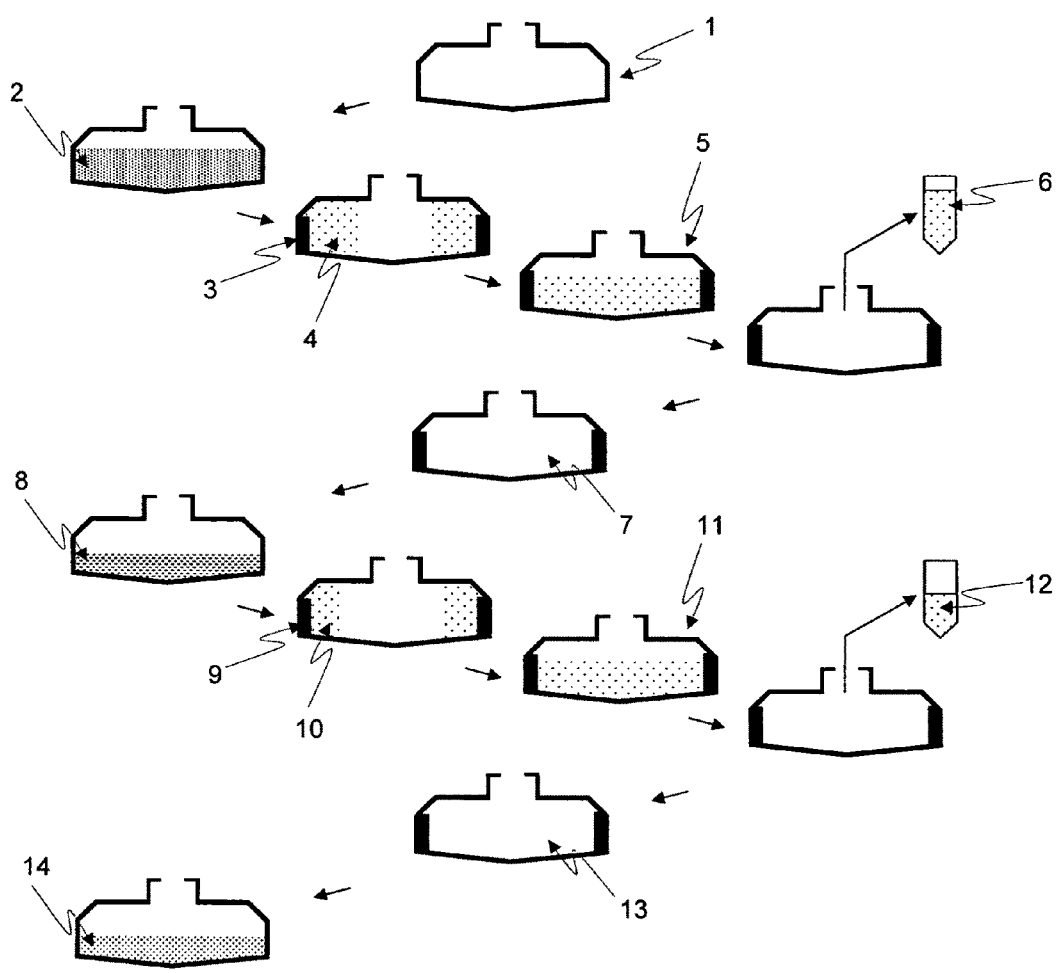
FIG. 3 illustrates the various steps generally used in the practice the method described herein.

FIG. 3 illustrates the various steps generally used in the practice the method described herein. While this illustration demonstrates the use of the removable receptacle in the practice of the method and does not show the associated horizontally rotatable hollow disk, it should be implied that the associated horizontally rotatable hollow disk is used in the practice of the method together with the removable receptacle. While this illustration demonstrates the use of the removable rotor in the practice of the method, this illustration is analogous to the use of the horizontally rotatable hollow disk described above and in FIGS. 1-1c.

An empty removable receptacle 1 is loaded with an initial suspension of particles 2 in an extracting medium of specific density. The receptacle is subjected to a specific centrifugal force for a specific amount of time. Those particles having densities greater than the density of the loaded extracting medium are deposited on the vertical wall 3 of the sedimentation chamber, while those particles with density equal to or lower than the density of the extracting medium remain suspended 4. The receptacle is decelerated allowing the suspended particles to reorient to a horizontal orientation 5. The particle suspension is removed from the receptacle and retained as the first extract 6. To the receptacle, containing particles on its walls is added an extracting medium 7 of a different specific density. Generally this extracting medium is of higher density than the previous extracting medium. The particles deposited on the walls are resuspended 8 by agitation. This agitation may be vortexing, stirring or other means. The receptacle is subjected to a specific centrifugal force for a specific amount of time. Those particles having densities greater than the density of the loaded extracting medium are deposited on the vertical wall 9 of the sedimentation chamber, while those particles with density equal to or lower than the density of the extracting medium remain suspended 10. The receptacle is decelerated allowing the suspended particles to reorient to a horizontal orientation 11. The particle suspension is removed from the receptacle and retained as the second extract 12. To the receptacle, containing particles on its walls is added an extracting medium 13 of a different specific density. Generally this extracting medium is of higher density than the previous extracting medium. The particles deposited on the walls are resuspended 14 by agitation. This agitation may be vortexing, stirring or other means. This process may be repeated iteratively until the desired fractionation is achieved.

The extracting medium is usually a defined mixture of sucrose and distilled and deionized water containing a salt buffer well-known to those skilled in the art. Typical salt buffers include 10 mM HEPES, 10 mM KCl, and 1 mM EDTA. Other salts suitable for use include Tris-HCl, NaCl, CHAPS, et al. The amount of sucrose used can vary between 4 to about 75 percent by weight of an aqueous solution. Other sugars, such as mannose, fructose or glucose can be substituted for sucrose in practicing the invention. Further, compounds such as cesium chloride or potassium bromide may be substituted for sucrose in the preparation of an extracting medium.

Synthetic reagents can also be substituted for sucrose in the preparation of the extracting medium. These include, but are not limited to, Percoll, Nycodenz, Optiprep™, NycoPrep™ Universal, Nycodenz™ and LymphoPrep™ (Available from Axis-Shield, Oslo, Norway).

Particles that may be isolated by the method described herein include, but are not limited to, human blood, human mononuclear cells, human monocytes and lymphocytes, polymorphonuclear leucocytes, human blood platelets, fractionation of neuronal cells, epithelial cells, human erythrocytes and reticulocytes, nuclei, lipid rich and other plasma membrane domains, ribonucleoproteins, DNA, RNA, plasma lipoproteins, lipo-polysaccharides, organelles and sub-cellular compartments, viruses, bacteria, high density lipoproteins, low density lipoproteins, and amyloid proteins.

Moreover, the use of the method described herein is useful for the determination of the presence of biomarkers in a particular tissue sample. The method described herein provides (1) a simple and reproducible technique for the fractionation of tissue lysates or cell homogenates, (2) a unique, statistical methodology for evaluation of potential biomarkers, and (3) the opportunity for generating data to enable the identification of positive margins in diseases such as cancer.

EXAMPLE 1

Subcellular Particle Fractionation and Proteomics Study of Rat Liver

Figure 4:
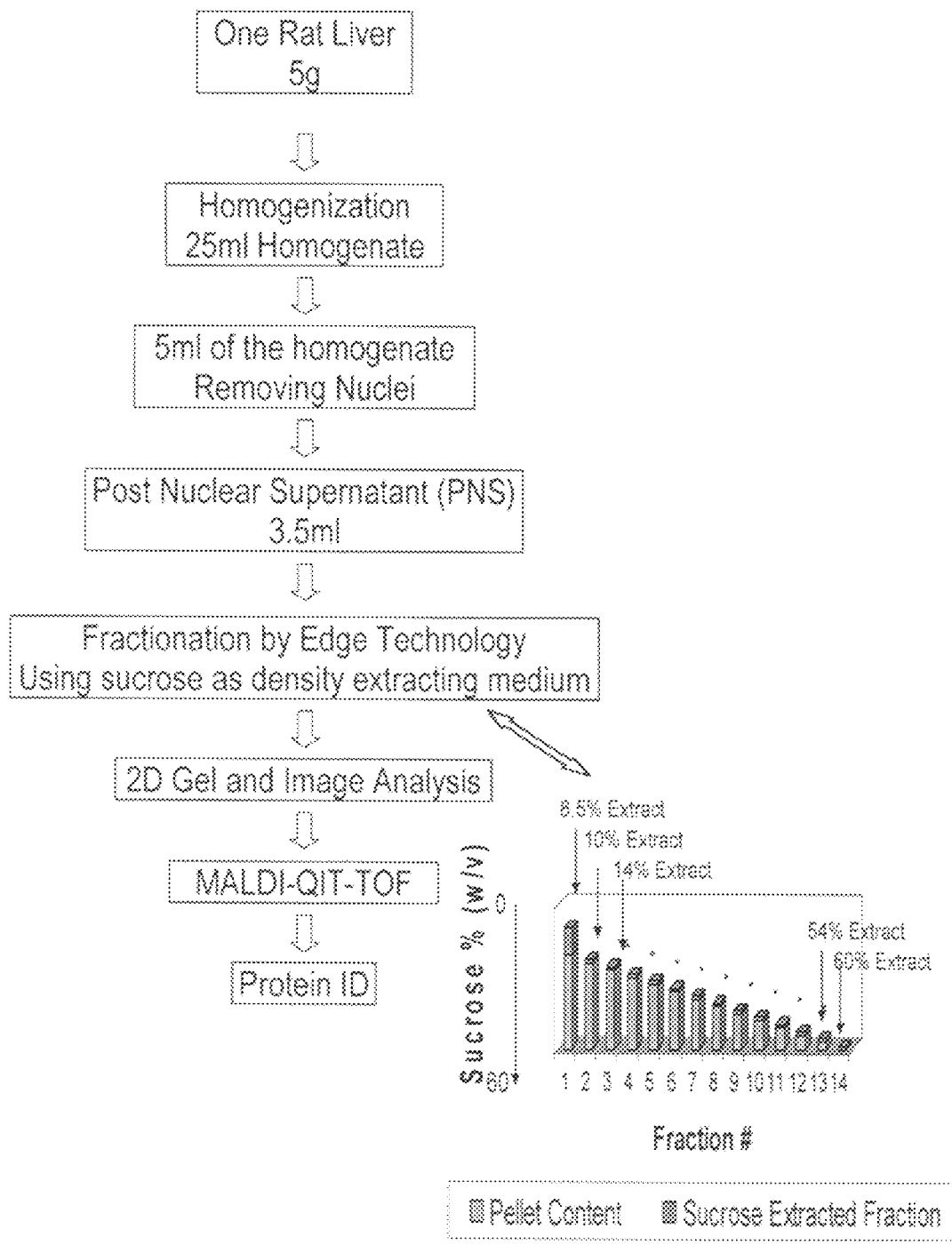
FIG. 4 illustrates the protocol used to perform a subcellular fractionation of rat liver and proteomics analysis.

The work flow of the rat liver subcellular fractionation and proteomics analysis is shown in FIG. 4.

I. Post Nuclear Supernatant Preparation: A rat liver post nuclear supernatant (PNS) from rat liver was prepared from a Sprague-Dawley rat (7-8 weeks of age). One frozen rat liver (about 5 g, Pel-Freez, Fayetteville, Ariz.) was thawed in 10 ml homogenization buffer (250 mM sucrose, 10 mM HEPES, 10 mM KCl, 1 mM EDTA, 10 µl protease inhibitor cocktail solution, pH 7.4) at 4° C. until the liver tissue turned soft. The thawed rat liver was diced into about 3 mm pieces with a pair of sharp scissors in the homogenization buffer. To the diced liver and homogenization buffer suspension was added an additional 10 ml of homogenization buffer. Half of the diced liver suspension was transferred to a prechilled 15 ml glass Dounce homogenizer. The rat liver was homogenized for 18-20 stokes using a loose pestle. The liver homogenate was transferred to a 50 ml tube. The second half of the diced liver suspension was homogenized using the same procedure, and was pooled together with the first batch of the homogenate and mixed well. The entire homogenization process was performed on ice. The volume of the total homogenate was about 25 ml. A 5 ml sample was removed from the total homogenate and was used for further processing. Nuclei were removed from this homogenate by low speed centrifugation (1000×g RCF) for 10 minutes using a fixed angle rotor. The nuclear pellet was discarded and the PNS (3.5 ml) was stored on ice for the following process.

II. Fractionation of the PNS: Prior to fractionation, 10 μl of the PNS was transferred to a separated container and used as a control sample for the analysis. Subsequently, a 2 ml sample of the PNS was loaded into a sedimentation chamber of a polyethylene receptacle having a volume of approximately 2.5 ml. This receptacle was then inserted into a horizontally rotatable hollow disk. The sedimentation chamber was accelerated to 91,000 revolutions per minute (rpm) in an air-driven centrifuge at air pressure of 35 psi. The centrifuge speed was maintained at 91000 rpm for 30 minutes. Following the 30 minute spin, the centrifuge was decelerated to the rest. The supernatant was aspirated from the polyethylene receptacle into a container, leaving a pelleted mass within the receptacle. The remainder of the PNS (1.5 ml) was loaded into the receptacle and the 91,000 rpm centrifugation step was repeated. The supernatant was aspirated from the receptacle, leaving additional pelleted mass, and was combined with the first supernatant. To the sedimentation chamber of the receptacle containing the combined pelleted masses was added 0.5 ml extract medium (10 mM HEPES, 10 mM KCl, 1 mM EDTA, pH 7.4) containing 10% sucrose (w/v). The receptacle then was vortexed for 5-6 minutes to suspend the pellet. The receptacle was inserted into the horizontally rotatable hollow disk. The sedimentation chamber was accelerated to 91000 rpm and maintained at that the speed for 2 minutes. After the centrifuge was decelerated to rest, the supernatant, the first extract fraction, was aspirated to a microcentrifuge tube for further analysis, leaving pelleted mass. To the sedimentation chamber of the receptacle containing the combined pelleted masses was added 0.5 ml extract medium (10 mM HEPES, 10 mM KCl, 1 mM EDTA, pH 7.4) containing 14% sucrose (w/v). The receptacle then was vortexed for 30-60 seconds to suspend the pellet. Then the receptacle was inserted into the horizontally rotatable hollow disk, which was accelerated to 91000 rpm. This extraction process was repeated using extract medium containing incrementally increasing amounts of sucrose (w/v)—18%, 22%, 26%, 30%, 34%, 38%, 42%, 46%, 48%, 52%, 56%, and 60%—to obtain a total of 14 extracted fractions including the first supernatant. The fractions were stored at 4° C. for further analysis.

III. Protein Assay: Protein concentration of each fraction, including the starting material PNS was determined using BCA assay kit from Pierce Biotechnology Inc, (Rockford, Ill.). (FIG. 5 shows the protein concentrations of the 14 fractions and PNS.)

IV. Two dimensional gel electrophoresis (2DE) and Gel Imaging analysis: PNS and four (4) fractions—14%, 26%, 38% and 46%—were selected for 2DE and imaging analysis. The fractions were first subjected to buffer exchange and reduction/alkylation. To each fraction, one volume of COMS solution (40 mM Tris, 7M Urea, 2M Thiourea and 1% C7 detergent) was added, and samples were reduced with tributylphosphine and alkylated with acrylamide followed by ultra-filtration in an Amicon ultra 10 kD cutoff spin column. The >10 kD fraction was then precipitated with nine volumes of acetone. The precipitated protein was solubilzed in resuspension reagent (7M Urea, 2M Thiourea and 2% CHAPS), quantitated by the Bradford assay and 100 g of each sample was subjected to isoelectric focusing (IEF) on 11 cm IPG strips (Bio-Rad, Hercules, Calif.) with an 3-10 pH range. Following IEF, IPG strips were equilibrated in 6M urea, 2% SDS, 50 mM Tris-acetate buffer (pH 7.0), 0.01% bromophenol blue and subjected to SDS polyacrylamide gel electrophoresis on Bio-Rad 8-16% criterion gels. Gels were then fixed in 10% methanol/7% acetic acid for two hours and stained overnight in Sypro Ruby followed by destaining in 10% methanol/7% acetic and imaged on the Bio-Rad gel doc. Images were subjected to image analysis using PG240 software from Nonlinear Dynamics (Nonlinear USA, Durham, N.C.). FIG. 6 shows the 2D gel image of the 4 fractions and PNS as well as the histogram of the protein spot 624 from 2D gel image analysis.

V. Selected gel spot cutting and in-gel digestion: Five anchor spots and five spots of interest from the 2D gels were excised by Bio-Rad EXQuest gel cutter. Each gel piece was transferred to an individual microcentrifuge tube. The gel pieces were first washed with 30% acetonitrile in 0.1 M ammonium bicarbonate for 10 minutes to remove the gel stain, and then washed with water and dried with speedvac evaporator. The pieces were swollen with 40 μl of 3 mM Tris-HCl, pH 8.8, containing 0.2 μg trypsin (Promega, Madison, Wis.). Digestion was performed for 12 hours at room temperature.

Figure 7:
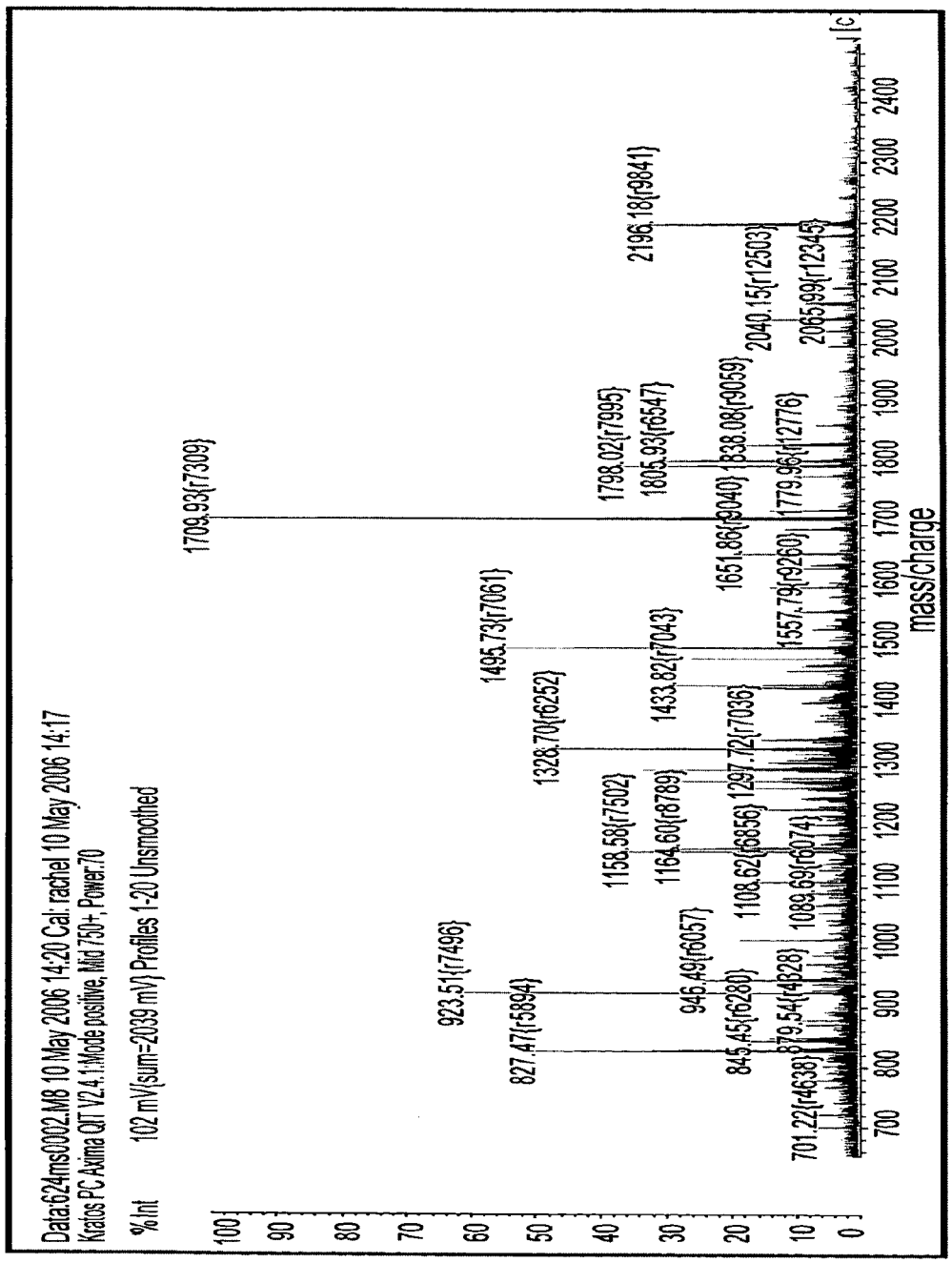
FIG. 7 illustrates the MALDI-QIT-TOF spectrum and MS/MS spectra of protein spot 624.
Figure 7:
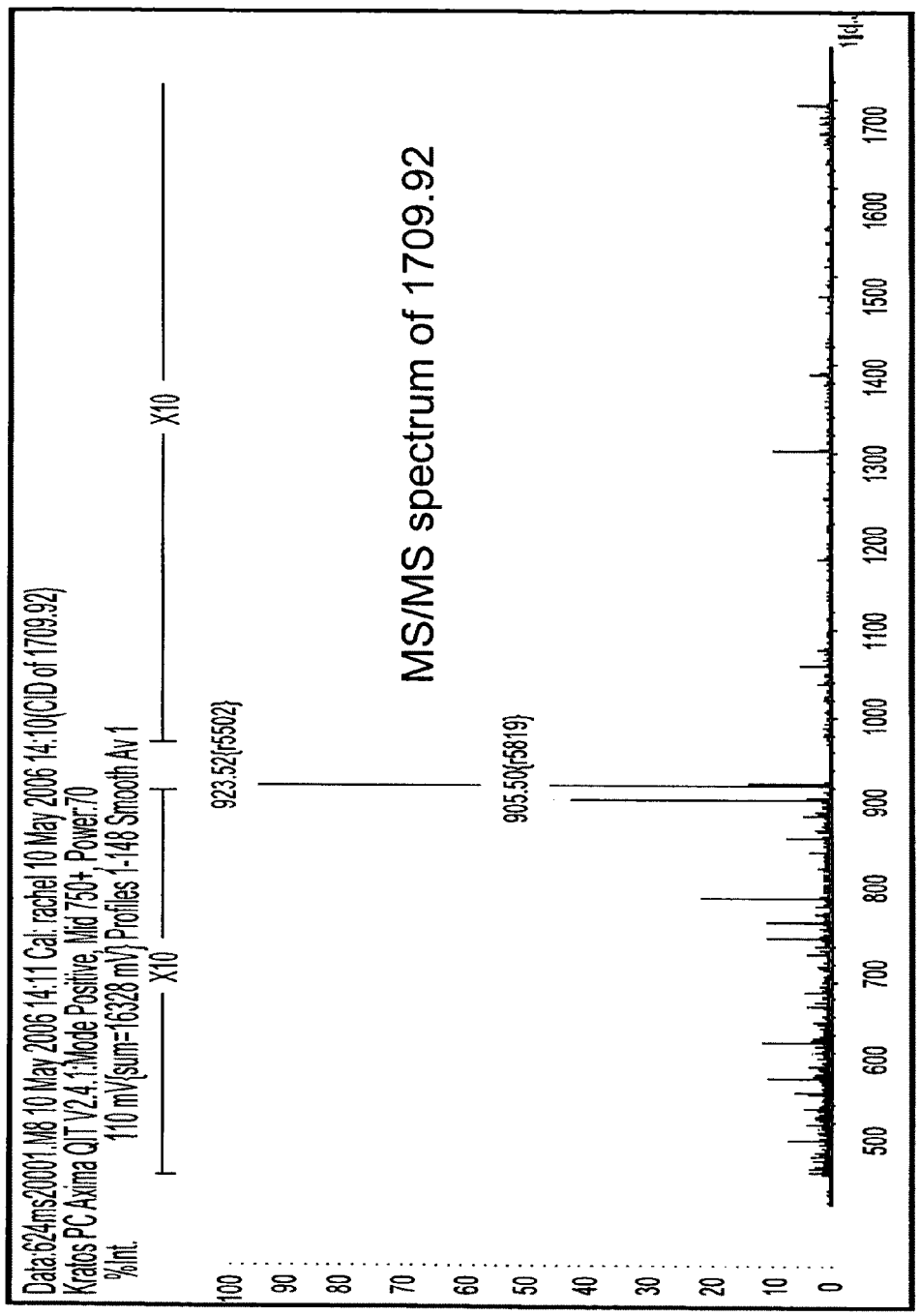
Figure 7:
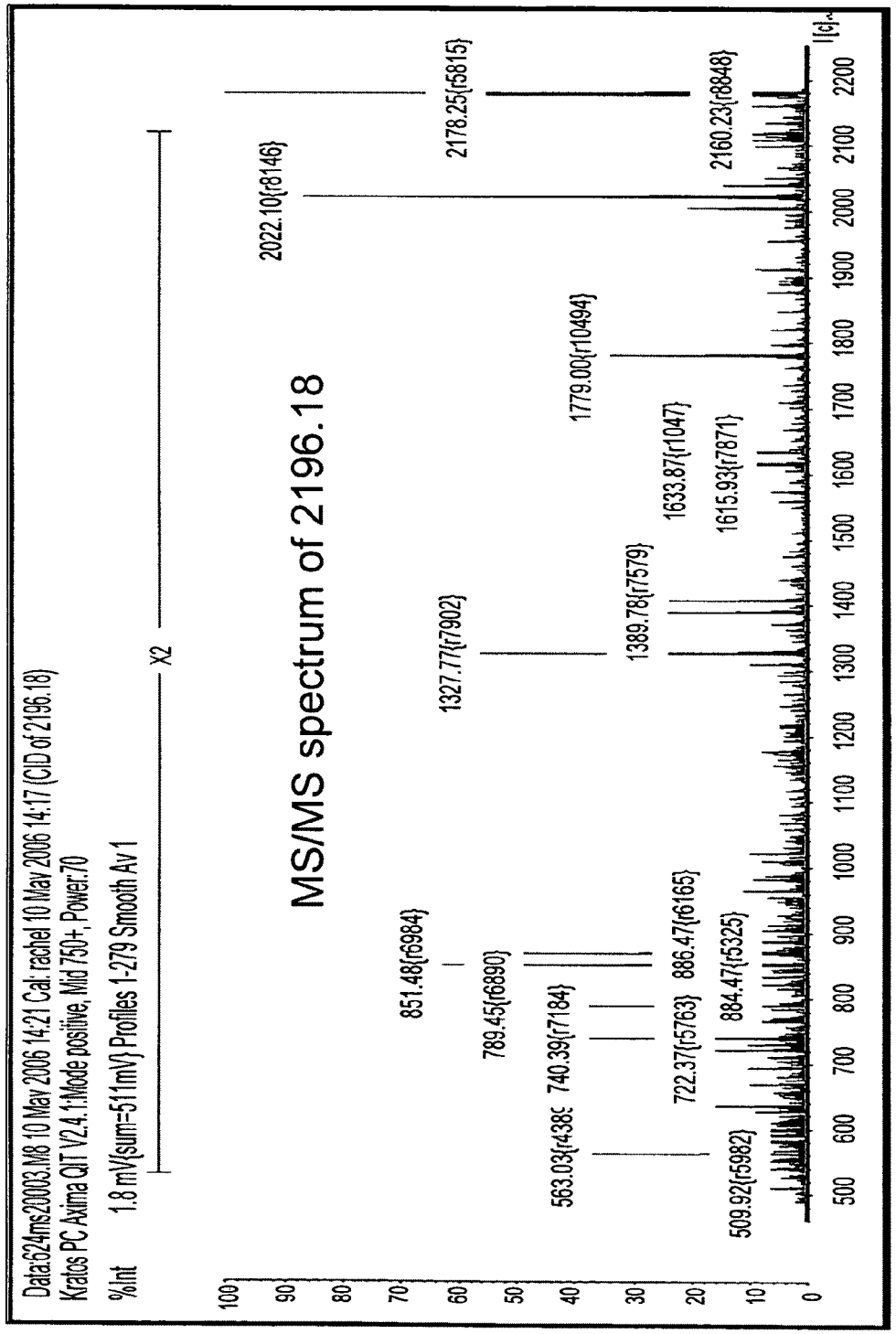

VI. Mass spectrometry (MALDI-QIT-TOF): The digested fractions were first purified via micro Zip Tipping. Briefly, the samples were dried down to a 10 μl volume and acidified with 1-2 μl of 1% trifluoroacetic acid (TFA). The samples were then loaded on an uC18 Zip Tip (Millipore Corp, Billerica, Mass.) after pre-equilibration in 0.1% TFA. After washing with 2×10 μl aliquots of 0.1% TFA samples were deposited directly onto the MALDI sample target using 1 μl of matrix solution 15 mg/ml of 2.5 dihydroxybenzoic acid in 50:50 acetonitrile: 0.1% TFA. Samples were allowed to air dry prior to insertion into the mass spectrometer. Analysis was performed on a Kratos Axima QIT (Shimadzu Scientific Instruments, Columbia, Md.) matrix-assisted-laser desorption/ionization (MALDI) mass spectrometer. Peptides were analyzed in positive ion mode in mid mass range (700-3000 Da). The instrument was externally calibrated with P14R (1533.86 Da) and ACTH (18-39)2465.20 Da. Precursors were selected based on signal intensity at a mass resolution width of 250 for CID fragmentation using Argon as the collision gas. (FIG. 7 shows the MALDI-QIT-TOF spectrum and MS/MS spectra of protein spot 624). Database searches were performed in house with Mascot (Matrix Sciences, Ltd., Boston, Mass.) using the Peptide Mass Fingerprint program for MS data and the MS/MS Ion Search program for CID data. Typically low abundant samples provide an insufficient number of peptides to make an identification based solely on MS information. All identifications were confirmed or established with CID (MS/MS) data. The protein spot 624 was identified as a hypothetical protein, which the protein has not discovered before except its gene sequence.

This method could be used for another application described as follows:

EXAMPLE 2

Virus Particle Separation from BmMLV

I: BmMLV virus preparation: Silkworm larvae (Kinshu.times.Showa strain) are injected at day 1 in the fifth instar with 150 μl of virus solution (equivalent to $1.0 \times 10^8$ BmN cells) in phosphate-buffered saline (PBS). The virus solution is prepared as follows: $1.6 \times 10^8$ BmN cells are homogenized in 75 ml of PBS and centrifuged at 7,000×g for 15 min at 4° C. After centrifugation, the supernatants are filtered (0.22-μm-pore-size filter) and used as the virus solution. BmN cells are harvested silkworm larvae, washed with PBS, and sonicated in 20 volumes of PBS. After low-speed centrifugation, the supernatants are filtered (0.22-μm-pore-size filter) and concentrated with an Amicon Ultra filter (Millipore).

II: BmMLV virus particle separation: The concentrated virus solution is subjected to the instant particle fractionation method using cesium chloride (CSCl) in buffer solution (10 mM Tris, 2 mM EDTA, pH 7.4) as an extracting density medium. The concentrated virus solution is initially suspended in the extracting medium containing 35% (w/v) CsCI. The virus suspension is transferred into a sedimentation chamber of a polyethylene receptacle, and the receptacle is inserted to a horizontally rotatable hollow disk. The sedimentation chamber is accelerated to 91,000 revolutions per minute (rpm) in an air-driven centrifuge at air pressure of 35 psi. The centrifuge speed is maintained at 91000 rpm for 30 minutes. Following the minute spin, the centrifuge is decelerated to the rest. The supernatant is aspirated from the polyethylene receptacle into a container, leaving a pelleted mass within the receptacle. To the sedimentation chamber of the receptacle containing the pelleted masses is added 0.5 ml the first extract medium containing 38% CsCI (w/v). The receptacle then is vortexed for 5-6 minutes to suspend the pellet. The receptacle is inserted into the horizontally rotatable hollow disk. The sediemntation chamber is accelerated to 91000 rpm and maintained at that the speed for 2 minutes. After the centrifuge is decelerated to rest, the supernatant, the first extract fraction, is aspirated to a microcentrifuge tube for further analysis, leaving pelleted mass. To the sedimentation chamber of the receptacle containing the pelleted masses is added 0.5 ml extract medium (10 mM HEPES, 10 mM KCl, 1 mM EDTA, pH 7.4) containing 43% CsCI (w/v). The receptacle then is vortexed for 30-60 seconds to suspend the pellet. Then the receptacle is inserted into the horizontally rotatable hollow disk, which is accelerated to 91000 rpm. This extraction process is repeated using extract medium containing incrementally increasing amounts of CsCl (w/v) 48%, 53%, 58%, 63%, 68%, 73%, 78%, 83%, 88%, 93%, and 98%, to obtain a total of 13 extracted fractions. The fractions can be stored at 4° C. for further electron microscopy analysis.

To demonstrate the utility of the described method in biomarker evaluation, rat models of high fat diet (HF) were used with control animals since a high fat diet has a profound effect on brain function and cardiovascular risk.

Figure 8:
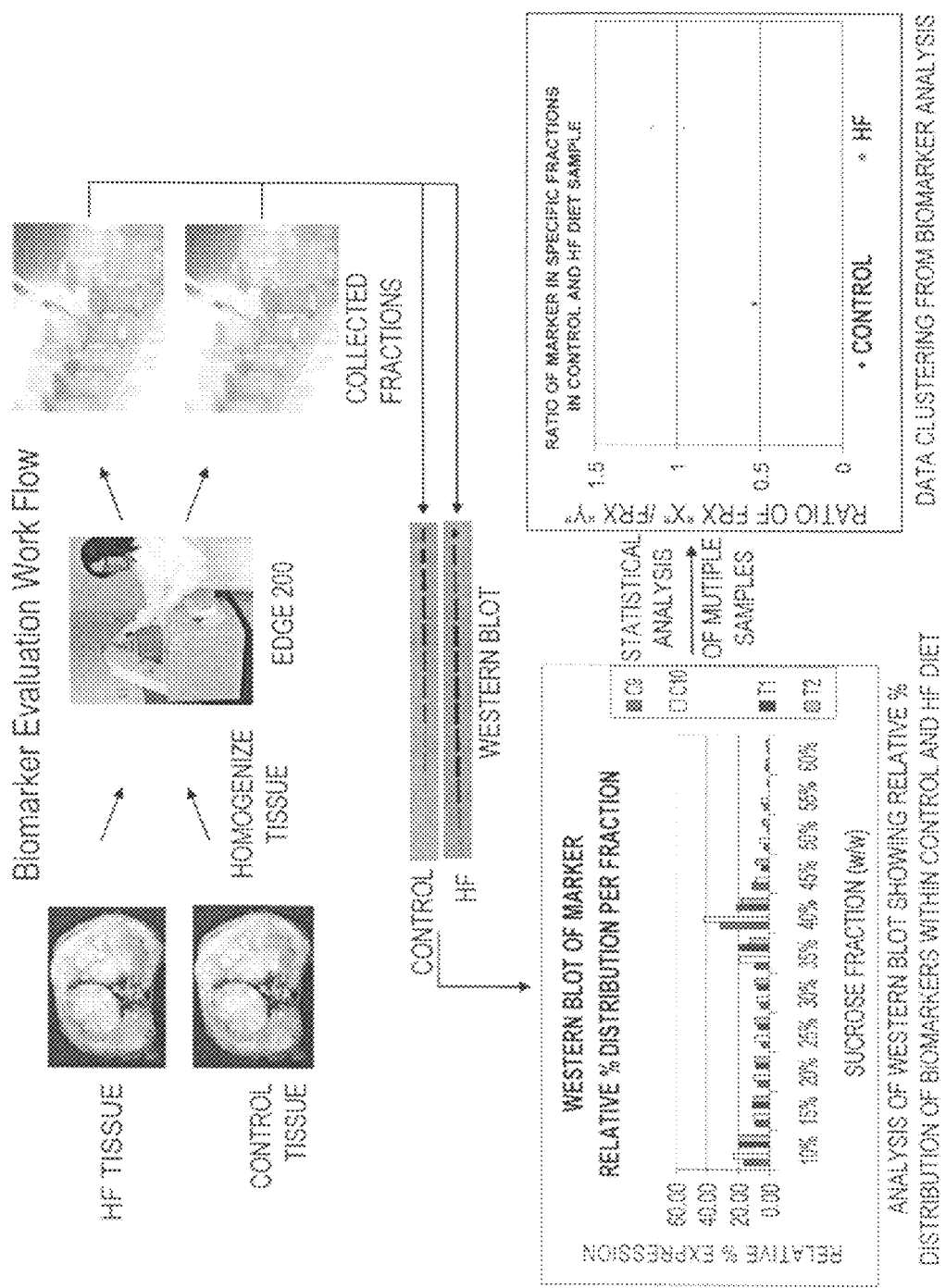
FIG. 8 illustrates the Biomarker evaluation work flow.

Twenty rats were separated into two groups of 10, one group fed with a special high fat diet for 6 weeks and one group fed with a regular low fat diet for the same time. Brains from each group were collected and snap frozen. Tissues were homogenized, then fractionated in accordance with the method described herein. All fractions from each sample were subjected to western blot analyses using synaptic dysfunction marker p-synapsin I. (Wu A, et al, Eur J. Neurosci. 2004 April; 19(7): 1699-707.) Results from each group were analyzed statistically. FIG. 8 shows the workflow of the experimental process.

Figure 12:
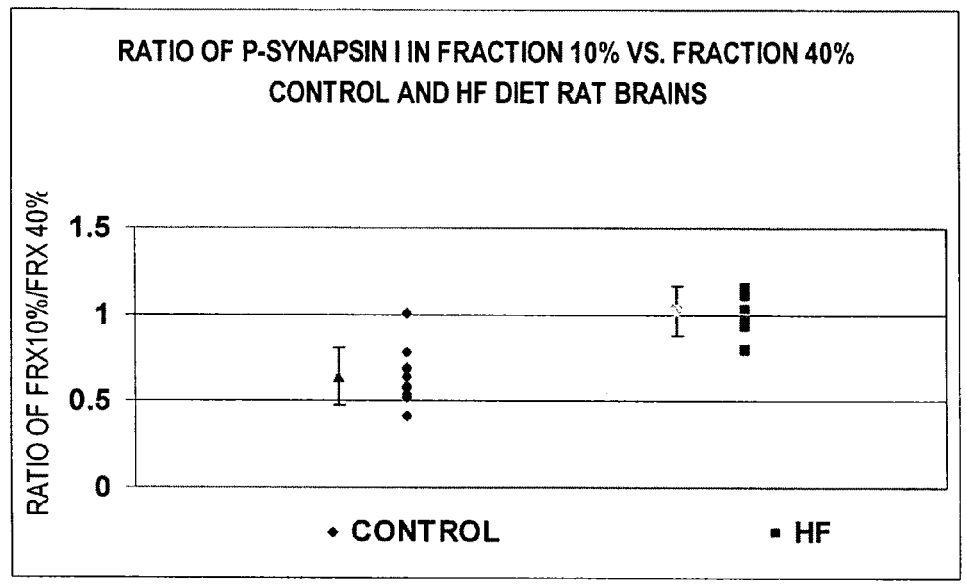
FIG. 12 illustrates in tabular and graphical form the ratios of p-synapsin relative expression in fraction 10% versus fraction 40% in brains from rats fed control and high fat diets.

A specific ratio of fractions (Frx) of (Frx 10%/Frx 40%) of p-synapsin I expression in control and HF diet rat brains based upon standard Western blot analyses as shown in FIG. 9. The results are shown in FIG. 12 in tabular and graphical form. The mean ratio and standard deviation (SD) are shown and error bars indicate a mean of plus or minus 1 SD.

Twenty-two rats were separated into two groups of 11, one group fed with a special high fat diet for 6 weeks and one group fed with a regular low fat diet for the same time. Hearts from each group were collected and snap frozen. Tissues were homogenized, then fractionated in accordance with the method described herein. All fractions from each sample were subjected to Western blot analyses using oxidative stress marker GRP75 (Carrido, C., et al., Cell Death and Differentiation, 2006, 13, 1423-1433.) Results from each group were analyzed statistically.

Figure 13:
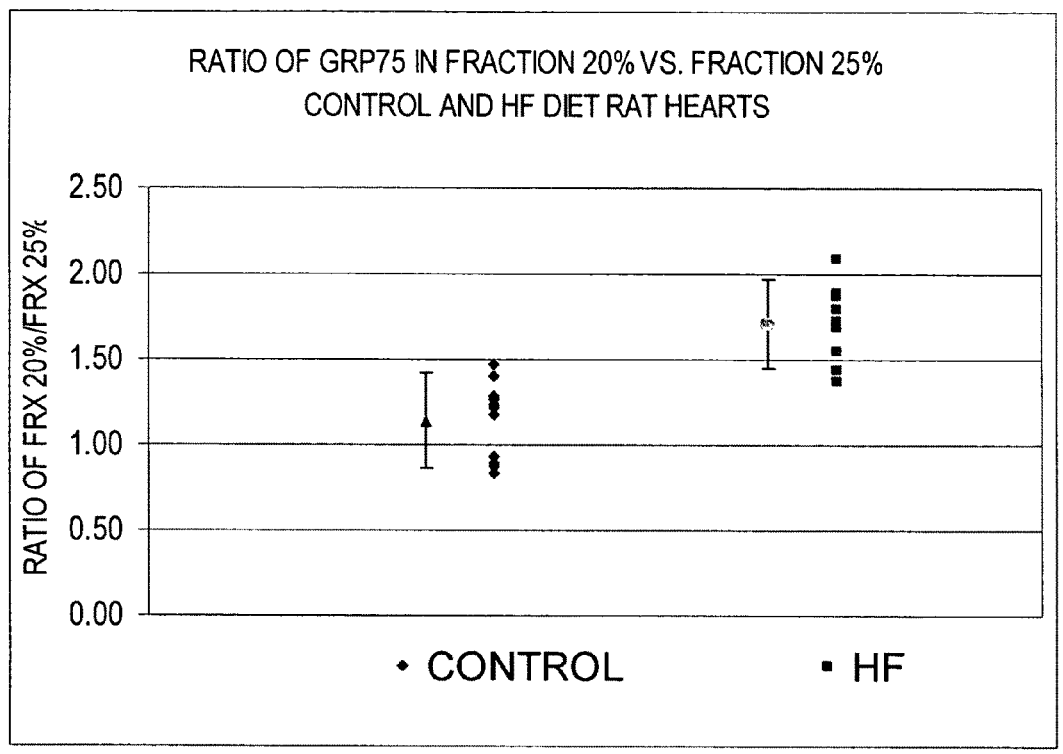
FIG. 13 illustrates in tabular and graphical form the ratios of GRP75 relative expression in fraction 20% versus fraction 25% in hearts from rats fed control and high fat diets.

A specific ratio of fractions (Frx) of (Frx 20%/Frx 25%) of GRP 75 expression in control and HF diet rat brains based upon standard Western blot analyses as shown in FIG. 10. The results are shown in FIG. 13 in tabular and graphical form. The mean ratio and standard deviation (SD) are shown and error bars indicate a mean of plus or minus 1.25 SD.

Using the fractionation method described herein, two biomarkers, p-synapsin-I and GRP 75, were evaluated by the novel statistical analysis method described herein. The relative distributions within the isolated fractions of a sample were observed to be different between control and HF diet samples. The ratios of marker expressions between two specific fractions within a sample are different for control and HF diet samples, with relatively tight clustering of data for both markers. Non-genetically identical animals were used for the experiments described herein. It is expected that experimental results using genetically identical animals will yield an improved clustering of data.

Notably, the statistical analysis method used herein does not require the use of external or internal standards. Further, since the method relies on ratios between internal fractions of the sample, the method is independent of sample amount. The combination of the fractionation method with the statistical analysis method allows the determination of the ratio of biomarker expression between two specific fractions of a test sample. Comparison of the ratio of a selected biomarker(s) obtained from the test sample with the ratios obtained for the same biomarker(s) in control and HF diet samples can be reliably used to determine if the test sample is control or HF diet.

Furthermore, in order to demonstrate the utility of the method in the intraoperative pathological diagnosis of positive margins of cancer and other diseases, needle core biopsy samples from patients with and without prostate cancer were used.

It has been reported that glucose-regulated protein, GRP78, is related to several human cancers (Shu, C., et al; J. Cell. Physiology, 2007, 215 (3): 627-635). A recent study has demonstrated that GRP78 plays a crucial role in the development of prostate cancer by promoting cancer cell proliferation, mediating oncogenic signaling and protecting cancer cells against cell death resulting from the stress of tumor development (Shani, G., et al; Mol Cell Biol 2009, 28 (2): 666-677). Two groups of patients with and without prostate cancer, as determined by the pathological evaluation of their biopsy samples, were randomly chosen for this study. Two needle core biopsy samples, one from the right gland and other from the left gland, were combined and homogenized using a glass dounce. Nuclei were removed and the post-nuclear supernatants were fractionated into four subcellular fractions in accordance with the method described herein. All fractions from each sample were subjected to western blot analysis using the GRP78 marker.

Figure 11:
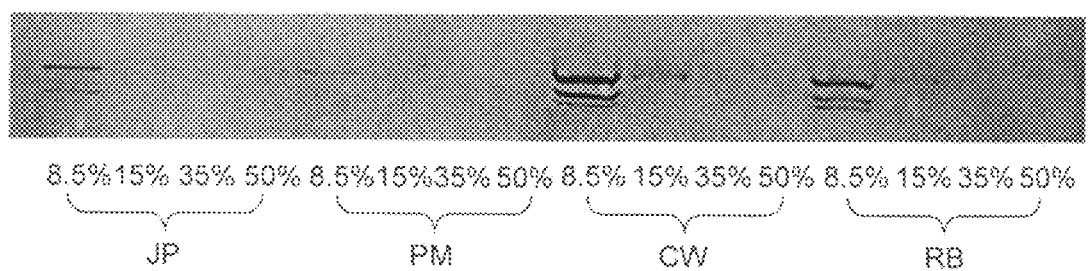
FIG. 11 illustrates the western blot of GRP78 of the prostate biopsy samples.
Figure 14:
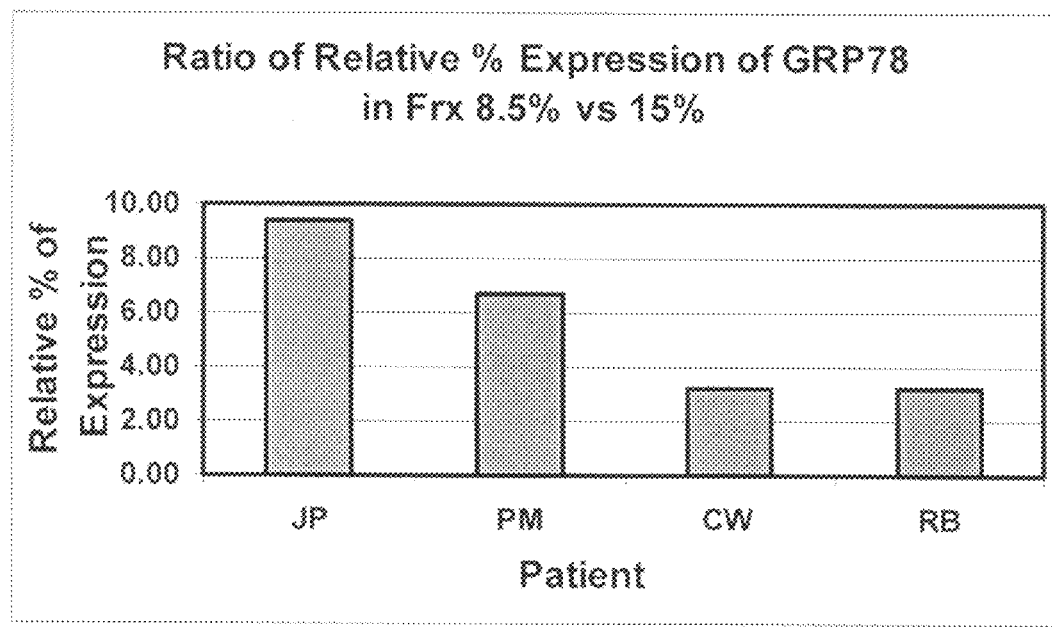
FIG. 14 illustrates in tabular and graphical form the ratios of GRP78 relative expression in fraction 8.5% versus fraction 15% in prostate tissue from men with and without positive biopsies for prostate cancer.

A specific ratio of fractions (Frx) of (Frx 8.5%/Frx 15%) of GRP 78 expression in cancer (CW and RB) and non-cancer (JP and PM) patients based upon standard western blot analyses is shown in FIG. 11. The results are shown in FIG. 14 in tabular and graphical form. Each western result was analyzed 5 times and the average result was used to generate the graphic.

The results indicate that the ratio of relative % expression of GRP78 derived from selected fractions is suppressed in patients with prostate cancer in comparison to patients free of the disease. Thus, the use of the instant method or system may be useful in the prognosis or diagnosis of prostate cancer from a test sample of human tissue or lysate thereof.

Additionally, this method or system can be used to rapidly evaluate and validate any potential biomarker candidates. Furthermore, this method or system can be extrapolated to the study of positive and negative margins in diseases such as prostate cancer. Comparison of the ratio of a selected biomarker(s) obtained from a biopsy specimen with the ratios obtained for the same biomarker(s) in negative margins and positive margins can be used to determine if the biopsy specimen represents a positive margin in an intraoperative manner. In this manner, a second surgery to remove cancerous tissue could be avoided.

EXAMPLE 3

Fractionation of Tissue Homogenates from Control and HF Diet Rats and Evaluation Potential Biomarkers: p-Synapsin I and GRP 75

I. Fractionation of Rat Brain and Heart tissue: The entire homogenization process was performed on ice. One frozen brain or heart was thawed in ice cold 1× homogenization buffer (20 mM HEPES, 1 mM $Na_2EDTA$ and 320 mM sucrose, pH 7.4 for brain; 20 mM HEPES, 10 mM KCl, 1 mM $Na_2EDTA$ and 250 mM sucrose, pH 7.4 for heart) with 0.01% v/v protease inhibitor cocktail. The tissue was dissected into 2-3 $mm^3$ pieces and the liquid was carefully discarded. The brain tissue pieces were resuspended in 5 volumes of brain homogenization buffer and the suspension was transferred to a glass homogenizer. The tissue was homogenized up-down 10 times by a loose pestle, and then followed by another 10 up-down times with a tight pestle. The crude homogenate was transferred to several centrifuge tubes and centrifuged at 800 g force for 10 minutes to remove nuclei. The supernatants, the post nuclear supernatant (PNS), from the tubes were pooled and the pellet was discarded. The PNS was kept on ice for further fractionation.

The heart tissue pieces were resuspended in 4 volumes of heart homogenization buffer and homogenization was performed as per brain tissue above. The PNS was generated as above, except that the pellet was not discarded. The pellet was resuspended in another 3 volumes of homogenization buffer. The tissue was homogenized up-down 20 times by a tight pestle. A second PNS was generated and combined with the first PNS and was kept on ice for further fractionation.

Edge 200 Separation System from Prospect Biosystems, Inc. (Newark, N.J.) was used for the density based fractionation. The fractionation procedure is summarized in the following steps: 1) 3 ml of PNS were transferred into a rotor sample container. 2) The rotor sample container was placed into a rotor, and spun at 95K RPM for 30 minutes for the brain sample, or for 2 minutes for the heart sample. 3) The rotor was decelerated to rest and the supernatant (S1) was collected, leaving the pellet on the container wall. 4) 10% density extraction media (1.5 ml for brain, and 0.5 ml for heart) was added into the rotor sample container, and the pellet was resuspended by vortexing. 5) The sample container was placed back into the rotor and was spun at 95K RPM for 2 minutes. 6) The rotor was decelerated and the supernatant was removed. 7) 0.5 ml of 15% density extraction media was added into the rotor sample container, and the pellet was resuspended by vortexing. 8) The sample container was placed back into the rotor and was spun at 95 K RPM for 2 minutes. 9) The rotor was decelerated and the supernatant was removed. 10) Steps 7-9 were repeated using sequentially increased density extraction media from 20-60%.

II. Western Blot Analysis of GRP 75 and p-Synapsin I: After fractionation, aliquots of the fractions and the PNS were diluted 3:1 with 4×SDS PAGE Reducing Sample Buffer containing 10% (v/v) of 2-mercaptoethanol. 50 ml of 4×SDS PAGE Sample Buffer was made by adding the following: 12.5 ml Milli-Q water, 12.5 ml 1 M Tris, pH 6.8, 20 ml Glycerol and 4 g SDS, and 20 mg Bromophenol Blue. The solution was mixed well by stirring and filtered using filter paper. Criterion 18-well 4-20% Tris-HCl gels and Tris/Glycine/SDS buffer (Bio-Rad) were used for electrophoresis. Electrophoresis was performed at constant 100 V until the dye front reached the end of the gel.

For Western blotting analysis, GRP75 was used to probe heart sample and p-Synapsin I was used to probe brain samples. Immuno-Blot PVDF membranes (Bio-Rad) were pre-soaked in methanol until translucent (~30 sec.). Following electrophoresis, the gels, PVDF membranes, filter papers and sponges (Bio-Rad) were soaked in transfer buffer (25 mM Tris base, 192 mM Glycine and 10% methanol) for 30 minutes before the transferring process. Transfer was done for 90 minutes at constant 1.0 mA for marker GRP75, and overnight at a constant 0.1 mA for marker p-Synapsin I. Membranes were blocked using 5% non-fat milk in TBS-T buffer: overnight at 4° C. for GRP75, or for 1 hour at room temperature (RT) for p-Synapsin I. For GRP75 western blots, a goat polyclonal antibody (Santa Cruz Biotechnology, Santa Cruz, Calif.) was used at 1:200 dilution for 1 hour at RT. For p-Synapsin I, a rabbit polyclonal antibody (Santa Cruz Biotechnology, Santa Cruz, Calif.) was used at either 1:100 or 1:200 dilution for 5 hours at RT. Donkey anti-goat IgG-HRP and goat anti-rabbit IgG-HRP (Santa Cruz Biotechnology) were used as secondary antibodies for GRP-75 or p-Synapsin I, respectively. Peroxidase activities were detected using Pierce's Metal Enhanced DAB substrate. The membranes were scanned using Umax PowerLook 1100 (Dallas, Tex.). The digitized images were analyzed using ImageJ software (NIH, Bethesda, Md.).

III. Statistical Analysis of Western Blot Results and Generation of a Ratio profile for Diagnostic and Marker Evaluation: Relative percentage of GRP75 and p-Synapsin I of each fraction for both control and high fat diet rat samples were calculated. Within each group of samples, either control or high fat, ratios of the relative percentage of the markers between two fractions were calculated for every possible combination of two fractions. The ratio from the specific two fractions which gave the biggest differences between control and high fat diet samples were selected based on the statistical analysis. The mean and standard deviation of the selected ratios within control and high fat diet rat samples were also calculated.

EXAMPLE 4

Fractionation of Prostate Needle Biopsy Homogenates from Cancer and Benign Human Samples and Evaluation of Potential Biomarkers: GRP 78

I. Fractionation of Prostate Needle Biopsy tissue: The entire homogenization process was performed on ice. Two needle core biopsy samples, one from the right gland and other from the left gland, were combined and thawed in ice cold 1× homogenization buffer (20 mM HEPES, 1 mM Na$_2$EDTA and 320 mM sucrose, pH 7.4) with 0.01% v/v protease inhibitor cocktail. The tissue was dissected into 2-3 mm$^3$ pieces and the liquid was carefully discarded. The tissue pieces were resuspended in 0.5 ml of homogenization buffer and the suspension was transferred to a glass tissue grinder. The tissue was homogenized up-down 20 times by a glass pestle. The crude homogenate was transferred to several centrifuge tubes and centrifuged at 800 g force for 10 minutes to remove nuclei. The supernatants, the post nuclear supernatant (PNS), was kept on ice for further fractionation and the pellet was discarded.

Edge 200 Separation System from Prospect Biosystems, Inc. (Newark, N.J.) was used for the density based fractionation. The fractionation procedure is summarized in the following steps: 1) PNS was transferred into a rotor sample container. 2) The rotor sample container was placed into a rotor, and spun at 95K RPM for 30 minutes. 3) The rotor was decelerated to rest and the supernatant was collected, leaving the pellet on the container wall. 4) 100 μl of 15% density extraction media was added into the rotor sample container, and the pellet was resuspended by vortexing. 5) The sample container was placed back into the rotor and was spun at 95K RPM for 2 minutes. 6) The rotor was decelerated and the supernatant was removed. 7) 100 μl of 35% density extraction media was added into the rotor sample container, and the pellet was resuspended by vortexing. 8) The sample container was placed back into the rotor and was spun at 95 K RPM for 2 minutes. 9) The rotor was decelerated and the supernatant was removed. 10) Steps 7-9 were repeated using 100 μl of 55% of extraction media.

II. Western Blot Analysis of GRP 78: After fractionation, aliquots of the fractions were diluted 3:1 with 4×SDS PAGE Reducing Sample Buffer containing 10% (v/v) of 2-mercaptoethanol. 50 ml of 4×SDS PAGE Sample Buffer was made by adding the following: 12.5 ml Milli-Q water, 12.5 ml 1 M Tris, pH 6.8, 20 ml Glycerol and 4 g SDS, and 20 mg Bromophenol Blue. The solution was mixed well by stirring and filtered using filter paper. Criterion 18-well 4-20% Tris-HCl gels and Tris/Glycine/SDS buffer (Bio-Rad) were used for electrophoresis. Electrophoresis was performed at constant 100 V until the dye front reached the end of the gel.

For Western blotting analysis, Immuno-Blot PVDF membranes (Bio-Rad) were pre-soaked in methanol until translucent (~30 sec.). Following electrophoresis, the gels, PVDF membranes, filter papers and sponges (Bio-Rad) were soaked in transfer buffer (25 mM Tris base, 192 mM Glycine and 10% methanol) for 30 minutes before the transferring process. Transfer was done for 90 minutes at constant 1.0 mA. Membranes were blocked using 5% non-fat milk in TBS-T buffer: overnight at 4° C. A goat polyclonal antibody (Santa Cruz Biotechnology, Santa Cruz, Calif.) was used at 1:200 dilution for 1 hour at RT. Donkey anti-goat IgG-HRP and goat anti-rabbit IgG-HRP (Santa Cruz Biotechnology) were used as secondary antibodies. Peroxidase activities were detected using Pierce's Metal Enhanced DAB substrate. The membranes were scanned using Umax PowerLook 1100 (Dallas, Tex.). The digitized images were analyzed using ImageJ software (NIH, Bethesda, Md.).

III. Statistical Analysis of Western Blot Results and Generation of a Ratio Profile for Diagnostic and Marker Evaluation: Relative percentage of GRP78 of each fraction for both cancer and benign samples were calculated. Within each group of samples, either cancer or benign, ratios of the relative percentage of the markers between two fractions were calculated for every possible combination of two fractions. The ratio from the specific two fractions which gave the biggest differences between cancer and benign samples were selected based on the statistical analysis.

Although the present invention has been described with reference to particular embodiments, it will be apparent to those skilled in the art that variations and modifications can be substituted therefore without departing from the principles of the invention.

We claim:

1. A method for the fractionation of cell lysates, tissue lysates, cell homogenates, or tissue homogenates contained in a sample into separate particles with different densities by centrifugal sedimentation in a centrifuge sedimentation chamber containing the sample suspended in a volume of an extracting medium of specific density such that said particles having a density less than or equal to said extracting medium will not sediment and said particles having a density greater than said extracting medium will move through the volume of the extracting medium, said method comprising the steps of:
   (a) delivering said sample to be analyzed as a suspension in said volume of an extracting medium of specific density to said sedimentation chamber;
   (b) spinning said centrifuge sedimentation chamber at the axis of rotation for a period of time between about 1 minute to about 2 hours at a centrifugal force between about 500 g to about 200,000 g;
   (c) allowing said particles having a density greater than said extracting medium of specific density to form a deposit on the inside wall of said sedimentation chamber;
   (d) removing the extracting medium from the sedimentation chamber to recover said particles having a density less than or equal to said extracting medium of specific density;
   (e) delivering to said sedimentation chamber a liquid volume of an extracting medium of a specific density that is different from that used in the extracting medium of step (c);
   (f) resuspending in said sedimentation chamber the deposited particles from step (c) by agitation with the extracting medium of step (e);
   (g) repeating steps (b)-(f) to isolate at least two fractions of different densities from said sample;
   (h) repeating steps (a)-(g) with a second sample to isolate at least two fractions of said second sample where the second sample fractions are the same densities as the fractions in step (g);
   (i) quantitatively analyzing one or more biomarkers within each of said fractions from steps (g) and (h) from each sample to obtain a value;
   (j) pairing the value for each fraction within a sample to the value for every other fraction within the sample to determine ratios between all pairs of fractions from step (g) and all pairs of fractions from step (h); and
   (k) comparing said ratios obtained from step (j) for the group of fractions from step (g) to said ratios obtained from step (j) for the group of fractions from step (h) to determine whether there is a statistical difference between said ratios.

2. The method of claim 1, where said time in step (b) is between about 1 to about 30 minutes.

3. The method of claim 2, where said time in step (b) is between about 1 to about 3 minutes.

4. The method of claim 1, where said centrifugal force in step (b) is between about 500 g to about 150,000 g.

5. The method of claim 4, where said centrifugal force in step (b) is between about 90,000 g to 110,000 g.

6. The method of claim 1, where said particles of step (d) are recovered by aspiration of the volume of the extracting medium in said centrifuge sedimentation chamber.

7. The method of claim 1, where said density of said extracting medium in step (e) is increased in equal increments at the completion of each repetition of step (d).

8. The method of claim 7, where said density of said extracting medium in step (e) is increased by about 0.0001 g/ml to about 0.2 g/ml at the completion of said repetition of step (d).

9. The method of claim 1, where said density of said extracting medium in step (e) is increased in unequal increments at the completion of each repetition of step (d).

10. The method of claim 9, where said density of said extracting medium in step (e) is increased by about 0.0001 g/ml to about 0.2 g/ml at the completion of said repetition of step (d).

11. The method of claim 1, where said volume of the extracting medium of specific density consists essentially of an aqueous mixture of a sugar and distilled, deionized water which contains a salt buffer.

12. The method of claim 11, where said sugar is selected from the group including sucrose, mannose, glucose and fructose.

13. The method of claim 11, where said aqueous mixture consists of about 4.0 to about 75% by weight per volume of sucrose or mannose.

14. The method of claim 1, where said liquid volume of extracting medium of specific density consists essentially of an aqueous mixture of a salt and distilled, deionized water.

15. The method of claim 14, where said salt is selected from the group consisting essentially of inorganic or organic salts of cesium, potassium and sodium.

16. The method of claim 15, where said salt is selected from the group consisting of cesium chloride, sodium bromide, and potassium bromide.

17. The method of claim 1, where said volume of extracting medium is from about 0.001 to about 50 milliliters.

18. The method of claim 17, where said volume of extracting medium is from about 0.050 to about 0.500 milliliters.

19. The method of claim 1, where said specific density in step (a) is from about 1.001 g/ml to about 2.0 g/ml.

20. The method of claim 1, where said sample is selected from the group consisting essentially of mammalian, plant, bacterial, yeast and fungal tissues and/or cells.

21. The method of claim 1, where said particle is a cell organelle.

22. The method of claim 21, where said cell organelle is the Golgi apparatus.

23. The method of claim 21, where said cell organelle is the mitochondria.

24. The method of claim 1, where said particle is the plasma membrane.

25. The method of claim 1, where said particle is a lipoprotein.

26. The method of claim 25, where said lipoprotein is high density lipoprotein (HDL).

27. The method of claim 25, where said lipoprotein is low density lipoprotein (LDL).

28. The method of claim 25, where said lipoprotein is very low density lipoprotein (VLDL).

29. The method of claim 1, where said deposit is not observable via total protein analysis.

30. The method of claim 1, where said centrifuge sedimentation chamber is defined as the physical space wherein the particles are deposited or remain suspended following application of a force.

31. The method of claim 30, where said physical space is within a horizontally rotatable hollow disk in a centrifuge.

32. The method of claim 30, where said physical space is within a removable receptacle that is inserted into a horizontally rotatable hollow disk in a centrifuge.

33. The method of claim 1, where said sample is from a rat, dog, mouse, or man.

34. The method of claim 1, where said biomarker in step (i) is p-synapsin I.

35. The method of claim 1, where said biomarker in step (i) is GRP 75.

36. The method of claim 1, where said biomarker in step (i) is GRP 78.

37. The method of claim 1, where said sample in steps (g) and (h) are derived from rat brain.

38. The method of claim 1, where said sample in steps (g) and (h) are derived from rat heart.

39. The method of claim 1, where said sample in steps (g) and (h) are derived from human prostate tissue.

40. The method of claim 1, where said quantitative analysis in step (i) is selected from the group consisting of, individually or in combination, Western Blot analysis, mass spectrometry, and ELISA.

41. The method of claim 1, further comprising the step of repeating steps (b)-(f) cyclically until the deposit of step (c) is not observable or a specific density of an extracting medium is reached.

42. A method for the fractionation of cell lysates, tissue lysates, cell homogenates, or tissue homogenates contained in a sample into separate particles with different densities by centrifugal sedimentation in a centrifuge sedimentation chamber containing the sample suspended in a volume of an extracting medium of specific density such that said particles having a density less than or equal to said extracting medium will not sediment and said particles having a density greater than said extracting medium will move through the volume of the extracting medium, said method comprising the steps of:

(a) delivering said sample to be analyzed as a suspension in said volume of an extracting medium of specific density to said sedimentation chamber;

(b) spinning said centrifuge sedimentation chamber at the axis of rotation for a period of time between about 1 minute to about 2 hours at a centrifugal force between about 500 g to about 200,000 g;

(c) allowing said particles having a density greater than said extracting medium of specific density to form a deposit on the inside wall of said sedimentation chamber;

(d) removing the extracting medium from the sedimentation chamber to recover said particles having a density less than or equal to said extracting medium of specific density;

(e) delivering to said sedimentation chamber a liquid volume of an extracting medium of a specific density that is different from that used in the extracting medium of step (c);

(f) resuspending in said sedimentation chamber the deposited particles from step (c) by agitation with the extraction medium of step (e);

(g) repeating steps (b)-(f) to isolate at least two fractions of different densities from said sample;

(h) repeating steps (a)-(g) with a second sample to isolate at least two fractions of said second sample where the second sample fractions isolated are the same densities as the fractions in step (g);

(i) quantitatively analyzing one or more biomarkers within each of said fractions from steps (g) and (h) from each sample to obtain a value;

(j) pairing the value for each fraction within a sample to the value for every other fraction within the sample to determine ratios between all pairs of fractions from step (g) and all pairs of fractions from step (h);

(k) repeating steps (a)-(g) with a test sample to isolate at least two fractions of said test sample where the test sample fractions isolated are the same densities as the fractions in step (g);

(l) quantitatively analyzing one or more biomarkers within each of said fractions from step (k) to obtain a value;

(m) pairing the value for each fraction within the test sample to the value for every other fraction within the test sample to determine ratios between all pairs of fractions from step (k); and (n) comparing said ratios obtained from step (j) for the group of fractions from step (g), the ratios obtained from step (j) for the group of fractions from step (h), and the ratios obtained from step (m) for the group of fractions from step (k) to determine whether there is a statistical difference among said ratios.

43. The method of claim 42, where said sample is from a rat, dog, mouse or man.

44. The method of claim 42, where said biomarker in step (i) is p-synapsin I.

45. The method of claim 42, where said biomarker in step (i) is GRP 75.

46. The method of claim 42, where said biomarker in step (i) is GRP 78.

47. The method of claim 42, where said sample in steps (g) and (h) are derived from rat brain.

48. The method of claim 42, where said sample in steps (g) and (h) are derived from rat heart.

49. The method of claim 42, where said sample in steps (g) and (h) are derived from human prostate tissue.

50. The method of claim 42, where said quantitative analysis in step (i) is selected from the group consisting of, individually or in combination, Western Blot analysis, mass spectrometry, and ELISA.

51. The method of claim 42, further comprising the step of repeating steps (b)-(f) cyclically until the deposit of step (c) is not observable or a specific density of an extracting medium is reached.

\* \* \* \* \*